United States Patent
Stark et al.

(10) Patent No.: US 7,416,537 B1
(45) Date of Patent: Aug. 26, 2008

(54) REHABILITATIVE ORTHOSES

(75) Inventors: John G. Stark, Deephaven, MN (US); Duane Oyen, Maple Grove, MN (US); Blair P. Mowery, Bloomington, MN (US)

(73) Assignee: IZEX Technologies, Inc., Minneapolis, MN (US)

( * ) Notice: Subject to any disclaimer, the term of this patent is extended or adjusted under 35 U.S.C. 154(b) by 0 days.

(21) Appl. No.: 09/339,071

(22) Filed: Jun. 23, 1999

(51) Int. Cl.
*A61H 1/02* (2006.01)

(52) U.S. Cl. .............................. 602/16; 602/19; 602/20; 602/23; 482/44; 482/900; 600/595

(58) Field of Classification Search .................... 602/5, 602/16, 19, 20–22, 23, 36, 27; 482/44, 100, 482/115–117, 139, 4, 5, 3, 7–8, 900; 600/8–9, 600/5, 595, 587
See application file for complete search history.

(56) References Cited

U.S. PATENT DOCUMENTS

| | | | |
|---|---|---|---|
| 3,521,623 A | 7/1970 | Nichols et al. | 128/78 |
| 3,667,457 A | 6/1972 | Zumaglini | 128/75 |
| 3,929,335 A * | 12/1975 | Malick | |
| 4,135,503 A | 1/1979 | Romano | 128/78 |
| 4,178,923 A | 12/1979 | Curlee | 128/78 |
| 4,306,571 A * | 12/1981 | McLeod, Jr. | |
| 4,436,099 A * | 3/1984 | Raftopoulos | 128/782 |
| 4,586,495 A | 5/1986 | Petrofsky | 128/82.1 |
| 4,621,620 A | 11/1986 | Anderson | 128/25 R |
| 4,645,199 A | 2/1987 | Bloemendaal | 272/73 |
| 4,653,479 A | 3/1987 | Maurer | 128/25 B |
| 4,711,242 A * | 12/1987 | Petrofsky | 602/16 |
| 4,762,134 A | 8/1988 | Gala | 128/781 |
| 4,801,138 A | 1/1989 | Airy et al. | 128/25 R |
| 4,825,852 A | 5/1989 | Genovese et al. | 128/25 R |
| 4,828,257 A | 5/1989 | Dyer et al. | 272/129 |
| 4,858,620 A | 8/1989 | Sugarman et al. | 128/774 |
| 4,863,157 A | 9/1989 | Mendel et al. | 272/73 |
| 4,912,638 A * | 3/1990 | Pratt, Jr. | |
| 4,934,694 A | 6/1990 | McIntosh | 272/129 |

(Continued)

FOREIGN PATENT DOCUMENTS

NL    7806327    12/1979

(Continued)

OTHER PUBLICATIONS

"A Prospective Short-Term Study of Chronic Low Back Pain Patients Utilizing Novel Objective Functional Measurement" by, Mayer et al., Pain, 25, 1986, pp. 53-68.

(Continued)

*Primary Examiner*—Steven O Douglas
(74) *Attorney, Agent, or Firm*—Dardi & Associates, PLLC; Peter S. Dardi

(57) ABSTRACT

Instrumented orthoses with more sophisticated structures provide for coordinated support and rehabilitation of complex joints and multiple injured joints. Improved instrumented orthoses can include hinges that can rotate in multiple different planes. Particularly preferred embodiments include a shoulder brace with a hand hold and a lower extremities brace. Preferably, a control unit monitors the output of transducers used to instrument the brace. A patient can be prompted by the control unit for the performance of a variety of different monitored exercises.

23 Claims, 8 Drawing Sheets

U.S. PATENT DOCUMENTS

| | | | |
|---|---|---|---|
| 4,958,632 A | 9/1990 | Duggan | 128/419 |
| 5,003,965 A | 4/1991 | Talish et al. | 128/24 AA |
| 5,012,820 A | 5/1991 | Meyer | 128/782 |
| 5,052,375 A | 10/1991 | Stark et al. | 128/25 R |
| 5,052,379 A | 10/1991 | Airy et al. | 128/80 |
| 5,078,152 A * | 1/1992 | Bond | |
| 5,181,902 A | 1/1993 | Erickson et al. | 600/13 |
| 5,195,941 A | 3/1993 | Erickson et al. | 600/14 |
| 5,239,987 A | 8/1993 | Kaiser et al. | 128/25 R |
| 5,255,188 A | 10/1993 | Telepko | 364/413.27 |
| 5,280,265 A * | 1/1994 | Kramer et al. | 338/210 |
| 5,282,460 A * | 2/1994 | Boldt | 601/13 |
| 5,284,131 A | 2/1994 | Gray | |
| 5,307,791 A | 5/1994 | Senoue et al. | 601/9 |
| 5,335,674 A * | 8/1994 | Siegler | |
| 5,360,392 A | 11/1994 | McCoy | 602/6 |
| 5,368,546 A | 11/1994 | Stark et al. | 601/34 |
| 5,437,610 A | 8/1995 | Cariapa et al. | 601/152 |
| 5,437,617 A | 8/1995 | Heinz et al. | 602/19 |
| 5,452,205 A * | 9/1995 | Telepko | 601/5 |
| 5,466,213 A * | 11/1995 | Hogan et al. | 601/33 |
| 5,476,441 A | 12/1995 | Durfee et al. | |
| 5,484,389 A * | 1/1996 | Stark et al. | 601/34 |
| 5,520,622 A | 5/1996 | Bastyr et al. | 602/16 |
| 5,569,120 A | 10/1996 | Anjanappa et al. | 482/4 |
| 5,597,373 A | 1/1997 | Bond et al. | |
| 5,662,693 A * | 9/1997 | Johnson et al. | 607/49 |
| 5,713,841 A | 2/1998 | Graham | 602/32 |
| 5,751,959 A | 5/1998 | Sato et al. | 395/200 |
| 5,788,618 A | 8/1998 | Joutras | 482/114 |
| 5,792,077 A * | 8/1998 | Gomes | 600/595 |
| 5,801,756 A | 9/1998 | Iizawa | 348/16 |
| 5,823,975 A | 10/1998 | Stark et al. | 600/595 |
| 5,827,209 A | 10/1998 | Gross | 602/19 |
| 5,954,621 A | 9/1999 | Joutras et al. | 482/114 |
| 5,980,435 A | 11/1999 | Joutras et al. | 182/114 |
| 6,296,595 B1 * | 10/2001 | Stark et al. | 482/91 |

FOREIGN PATENT DOCUMENTS

| | | |
|---|---|---|
| SU | 1380747 A | 3/1988 |
| SU | 1750681 A1 | 7/1992 |
| WO | WO 95/01769 | 7/1994 |

OTHER PUBLICATIONS

"Assessment of the Progress of the Back-Pain Patient" by, Million et al., Spine, vol. 7, No. 3, 1982.

"Put Your Patients Recovery Steps Ahead with the Sutter CPT™ 9000" by, Sutter Biomedical Inc., Product Literature, Jan. 1985.

Smith & Nephew Rolyan Product Literature.

1994 Thera-Kinetics Product literature.

"Upper Extremities and Back Product Literature" by, Smith & Nephew DonJoy, Inc. Rev. May 1996.

"Newport Shoulder System" Literature by, Orthodmerica Products, Inc., 1996.

"Masterhinge Shoulder Brace 3" Product Literature by, Johnson & Johnson Professional, Inc.

* cited by examiner

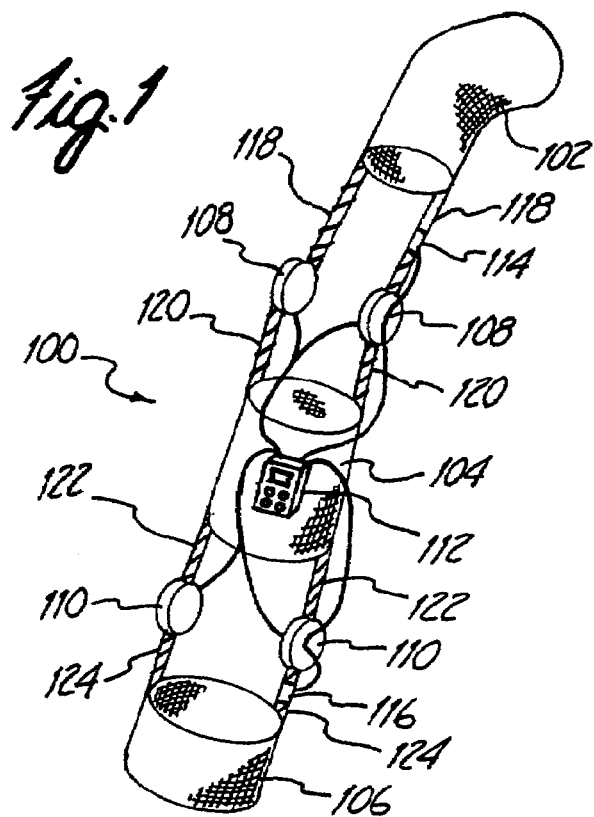
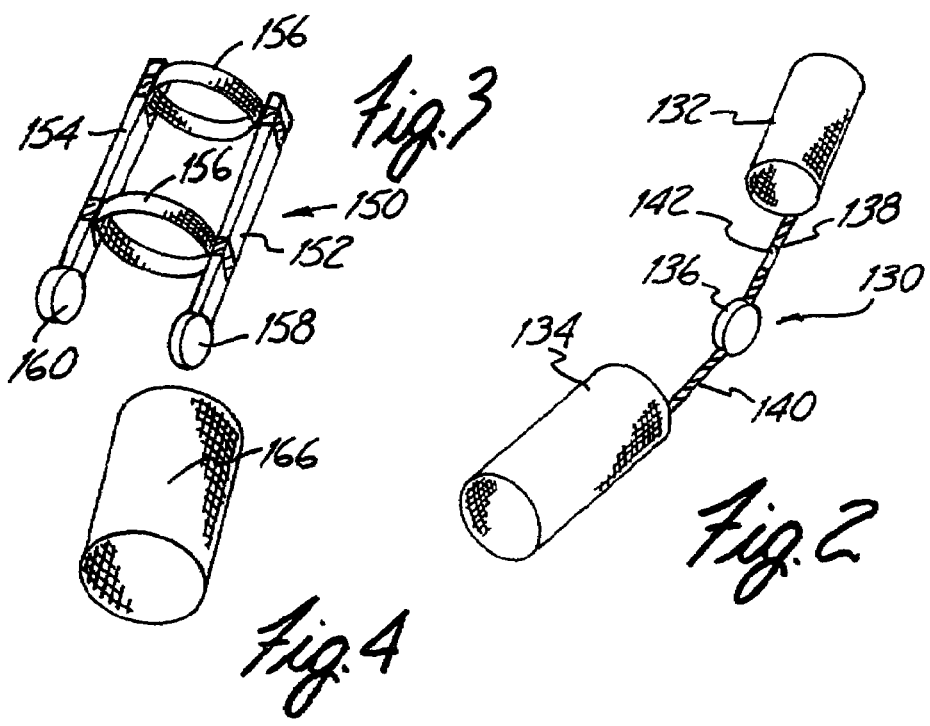

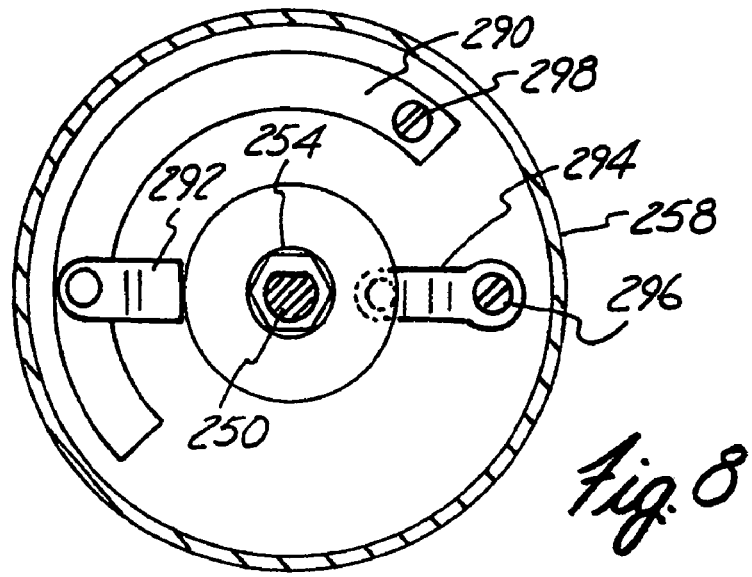
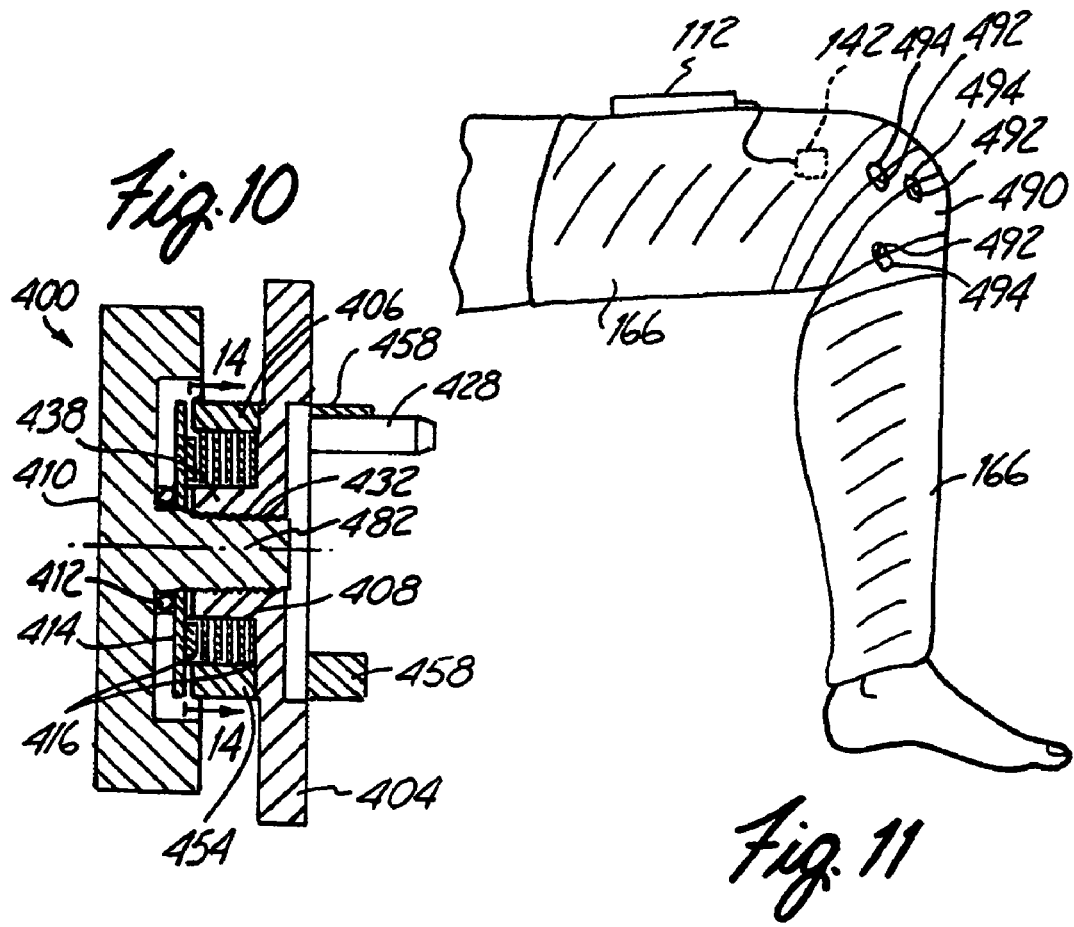

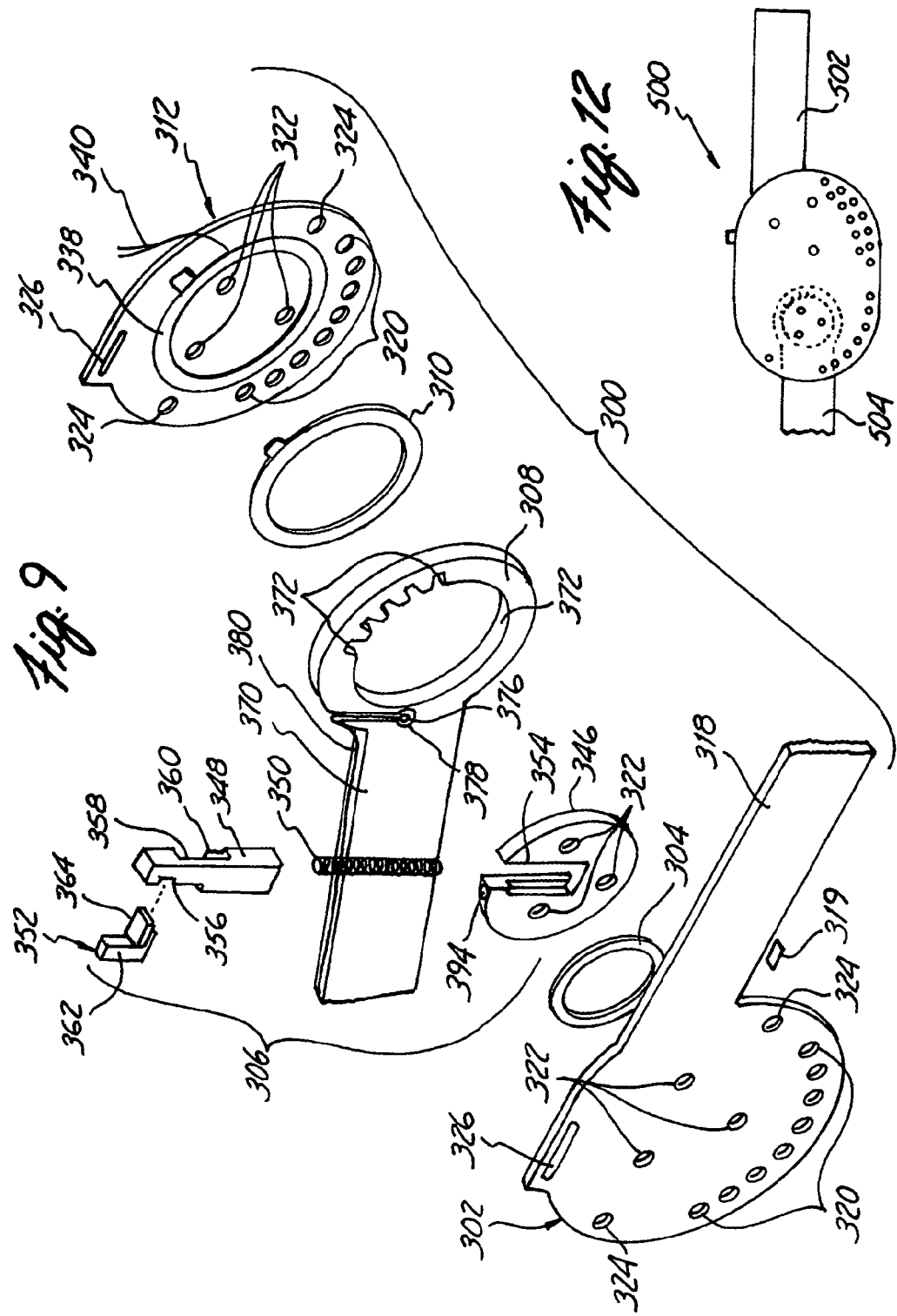

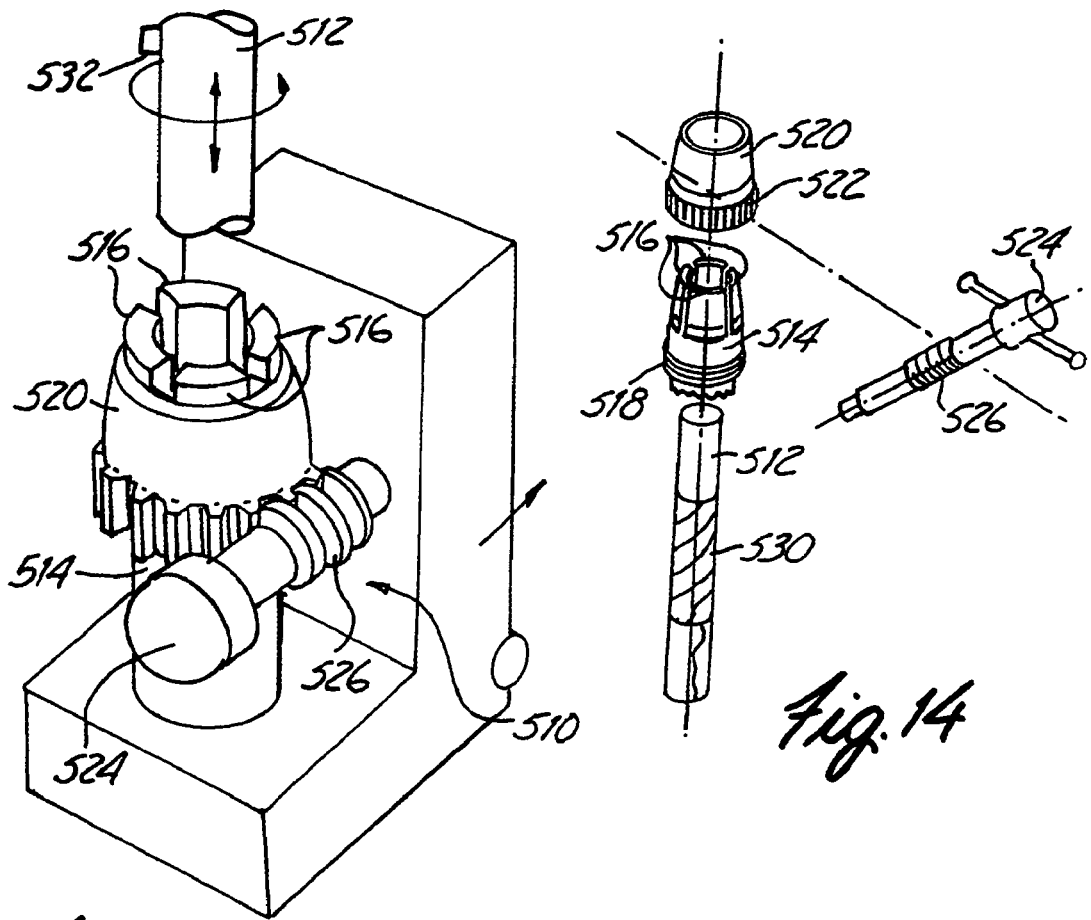
Fig. 13
Fig. 14
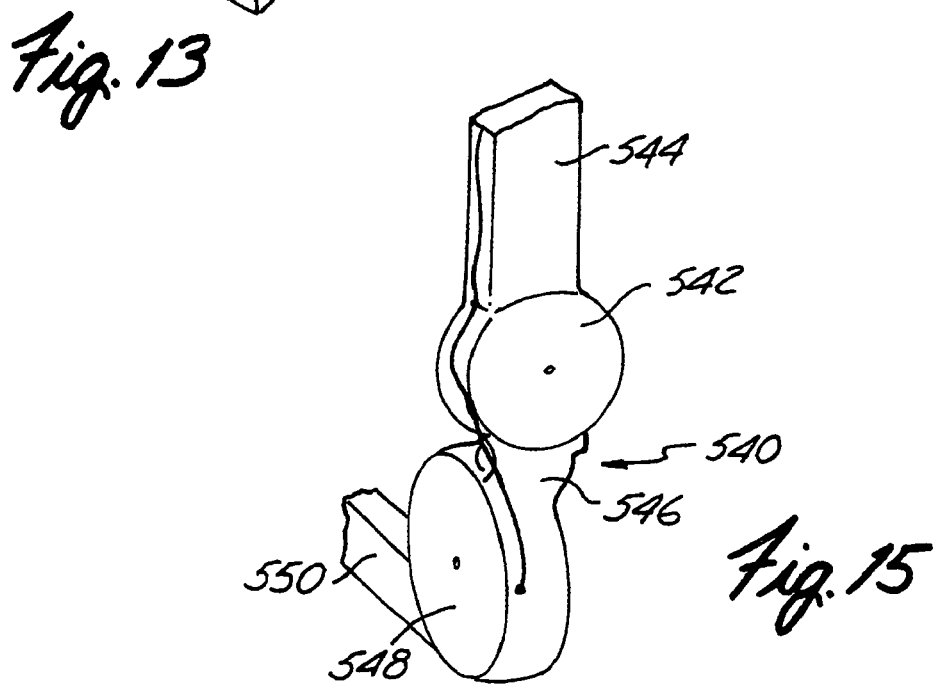
Fig. 15

REHABILITATIVE ORTHOSES

BACKGROUND OF THE INVENTION

The invention relates to orthoses useful for the rehabilitation of patients with injured joints, weakened joints, and/or neurological deficits degrading motor control or operation of joints. More particularly, the invention relates to instrumented orthoses for the performance of monitored rehabilitative exercises.

Both muscles and bones should be exercised to maintain strength. Also, bone fractures that are exposed to permissible weight bearing stress often heal more predictably and more rapidly than fractures that are not stressed at all. Improved healing based on application of appropriate stress is also believed to be true for connective tissue, such as ligaments and cartilage.

In the case of neurological injury or degradation, the nerve impulse pathways that control skeletal motor functions and joints are interrupted due to loss of brain cells or nerve conducting structures. Such neurological injuries can result from cerebrovascular accidents such as ischemic or hemorrhagic strokes or certain types of head trauma. Recovery mechanisms involve creation of new neurological pathways by retraining the motor functions with different surviving brain cells as receptors. This requires physical therapy and joint exercise very similar to exercise that is advantageous for rehabilitation of joints following orthopedic injury. Additionally, joint disuse following such neurological injury similarly requires orthopedic rehabilitation and stress to effect useful recovery, given the secondary orthopedic damage resulting from the disuse.

Suitable stress can be applied to the tissue by the performance of selected exercises. For example, isometric exercises generally involves the exertion of force against a relatively immovable object. To perform isometric exercises, a restraining device can be used that has a substantially unchanging position for the duration of a particular exercise routine. Isotonic exercises involve exertion against the same weight or resistance through a range of motion. Isokinetic exercise is designed to mimic exertions that take place on a playing field or the like. When performing isokinetic exercises in a simulated environment, a machine is used to provide resistance in direct proportion to the exertion of the exerciser.

Isometric exercises are particularly useful with painful injuries to lower the risk of further injury. If performed in a controlled manner, isometric exercises can be performed earlier in the recuperation period to speed recovery. As the patient's recovery progresses, isotonic exercises or other exercises can be used to reestablish a desired range of motion about a joint. With continuing recovery, eventually the patient is able to perform a full range of exercises.

A difficulty with the application of stress to an injured joint is that the application of excessive stress can further injure the joint rather than assist with the healing. Thus, the exercises need to be carefully planned to provide appropriate amounts of stress. Also, the performance of the exercises should be monitored closely by a physician, physical therapist or other appropriate health care professional to optimize the treatment and to reduce the risk of injury. The need to carefully plan and closely monitor the exercises provides a cost and motivation barrier to accessing desirable amounts of exercise.

SUMMARY OF THE INVENTION

In a first aspect, the invention pertains to an instrumented orthosis comprising:

a support that fits around the joint of a patient, the support comprising a hinge that can rotate in different planes;

a position sensor operably connected to the hinge such that motion can be measured with respect to different rotational motions about the joint; and a control unit operably connected to the position sensor to receive signals related to the position of the hinge.

In another aspect, the invention pertains to method of rehabilitating a joint that has a range of motion in a plurality of planes. The method involves exercising with an orthosis having a hinge that can rotate in different planes. The hinge preferably includes a position sensor that can provide measurement of the orientation of the hinge in the different planes. The orthosis includes a control unit connected to one or more position sensors.

In a further aspect, the invention pertains to an orthosis comprising:

a support that fits around a plurality of joints of a patient, the support comprising a plurality of hinges such that motions about separate hinges correspond to motions about different joints;

position sensors operably connected with the hinges such that motion can be measured about different joints; and a control unit operably connected to the position sensors to receive signals related to the position of the hinges.

Moreover, the invention pertains to a method of upper body rehabilitation comprising exercising two or more adjacent joints using an ambulatory orthosis supporting the two or more adjacent joints. The orthosis preferably is connected to a control unit that provides a target exercise routine and immediate feedback on patient performance relative to the target exercise routine with respect to motion about either of the adjacent joints.

In additional aspects, the invention pertains to a leg orthosis including:

an ambulatory support structure including:

a waist support;

an upper leg support;

a lower leg support;

a hinge connecting the waist support with the upper leg support;

a hinge connecting the upper leg support and the lower leg support;

sensors operably connected to the support structure to measure forces applied to the support structure; and a control unit connected to the sensors to receive measurements related to the applied forces.

In another aspect, the invention pertains to a method of rehabilitating a stroke victim including performing a set of exercises using an ambulatory orthosis supporting the hip and knee. The orthosis preferably is connected to a control unit that provides a target exercise routine directing the application of forces by the patient at the hip and knee and provides immediate feedback on patient performance relative to the target routine.

In a further aspect, the invention pertains to a shoulder orthosis including:

an ambulatory shoulder support;

a hand hold extending from the shoulder support;

a transducer operably connected to the hand hold such that forces applied to the hand hold result in an altered signal from the transducer; and a control unit connected to the transducer to receive measurements of forces applied to the hand hold.

The ambulatory shoulder support preferably includes a trunk support and an under arm support directly or indirectly connected to the trunk support by a hinge, preferably a multi-dimensional hinge.

In addition, the invention pertains to a method of evaluating a patient's mental condition comprising:
  collecting answers to a set of questions regarding the patient's mental condition using a remote controller programmed to pose the questions and receive the answers; and
  evaluation of the answers by a health care professional.

BRIEF DESCRIPTION OF THE DRAWINGS

FIG. 1 is a schematic perspective view of an orthosis for supporting two joints.

FIG. 2 is a schematic perspective view of an orthosis with a hinge capable of rotating in multiple planes.

FIG. 3 is a schematic perspective view of an embodiment of a support portion.

FIG. 4 is a schematic perspective view of an alternative embodiment of a support portion.

FIG. 8 is a sectional, side view of the electromechanical hinge of FIG. 7 taken along line 8-8.

FIG. 9 is an exploded, perspective view of an embodiment of a mechanical hinge with an easy to use locking mechanism.

FIG. 10 is a sectional front view of a manual resistance unit that can be used with the mechanical hinge of FIG. 9.

FIG. 11 is a side view of an orthosis with an articulating hinge connecting two support portions.

FIG. 12 is a side view of a mechanical, biaxial hinge.

FIG. 13 is a fragmentary, perspective view of one embodiment of a hinge that provides for motion in two planes.

FIG. 14 is an exploded, perspective view of the principle components of the hinge of FIG. 13.

FIG. 15 is a fragmentary, perspective view of an alternative embodiment of a hinge that provides for rotation in two planes.

DETAILED DESCRIPTION OF THE PREFERRED EMBODIMENTS

Figure 5:
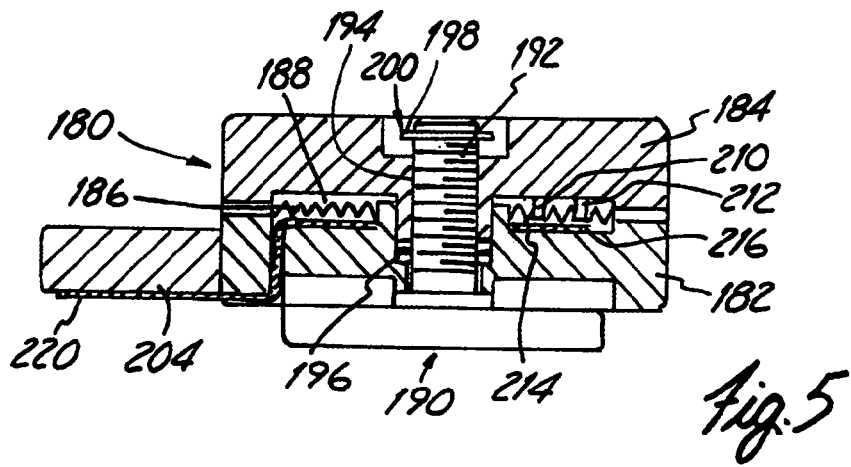
FIG. 5 is a sectional top view of a hinge with a mechanical locking feature and a position sensor, where the section is taken through the central axis of the hinge.

Sophisticated instrumented orthoses/braces provide for more complex and coordinated rehabilitation exercises than previously possible. In particular, certain embodiments are suitable for the rehabilitation of complex joints that enable motion in multiple, different planes. These complex joints can be rehabilitated much more efficiently and appropriately using the more sophisticated orthoses described herein. Furthermore, other embodiments of the improved orthoses are particularly suitable for the rehabilitation of stroke victims. These stroke braces provide suitable rehabilitation for patients that have lost motor function on one side or both sides of their body. Thus, the rehabilitation can involve muscle building as well as neuro-reflex retraining. Using these sophisticated orthoses, many serious injuries/illnesses can be treated more effectively than was possible previously and, potentially, at a lower cost.

Certain embodiments of the improved orthoses are suitable for the rehabilitation of joints that move in multiple planes of motion. Joints that move in multiple planes of motion include, for example, shoulder, spine, hip, wrist and ankle/foot. These orthoses include a support structure that fits around the joint and supports the body portions connecting at the joint. The support structure includes one or more hinges that provide for motion of the joint in multiple planes of motion. Position sensors preferably provide for measurements of the position of the hinge in the multiple planes of motion. The hinge or hinges preferably provide for the measurement of the motion about two or more planes of motion. The orthoses can include additional types of transducers, such as strain gauges. Preferred embodiments include instrumented shoulder braces that provide for the multiple planes of, motion of the shoulder. Preferred shoulder braces can further include instrumented supports for the arm, elbow and/or hand.

Certain embodiments of the improved orthoses are particularly suitable for use as a stroke brace. Stroke victims can lose a significant portion of their motor control on one or both sides of their body. These victims need a particularly high level of support and can benefit tremendously from appropriate type of rehabilitative exercises. Because stroke victims generally have injuries that involve multiple joints, a stroke brace includes a support structure that provides support for multiple joints. Preferred stroke orthoses include an upper extremity brace along with a long leg brace, although other embodiments can be used. In preferred embodiments, the support structures include hinges providing for motion of multiple joints.

The hinges preferably include position sensors for measuring the motion about the hinge. The orthoses can include additional types of transducers, such as strain gauges. The orthosis can provide for multiple planes motion about one or more of the joints. The instrumentation of the orthosis generally involves a control unit that is operably connected to transducers on the orthosis. The control unit can be used to provide feedback and instructions to the patient to assist with the retraining of neurological pathways. Instrumentation of the orthosis reduces the need for professional intervention.

Hand injuries may not be adequately treated by standard types of orthoses with hinges. Furthermore, hand muscles can atrophy due to inactivity following an arm injury. An improved hand orthosis includes an instrumented squeeze device, such as an air-bulb or a foam grip. Generally, the instrumented squeeze ball is supported by a support that extends, at least, to the patient's wrist. In certain embodiments, the instrumentation measures the total force exerted by the hand onto the squeeze ball. In other embodiment, the instrumentation provides for measurements of forces applied by individual fingers. The capability to measure the force exerted by individual fingers is particularly suitable for a stroke brace where redevelopment of neuromuscular control of the movement of individual fingers is a significant consideration.

As noted above, preferred embodiments of the improved orthoses include a control unit operably connected to transducers placed on the orthosis for position, strain or other measurements. The control unit preferably includes a microprocessor to assist with the monitoring of the rehabilitative exercises. Information regarding the compliance and performance of the patient can be downloaded from the control unit for evaluation by a health care professional. Microprocessor based control units can provide instruction to and prompting of the patient for the performance of the selected exercises. The selection of suitable exercises preferably is performed by a health care professional following an examination of the condition of the patient. The control unit is programmed accordingly.

1. Orthosis Structure

Previous instrumented orthoses are designed for placement around a single joint. Support portions support the respective body portions that meet at the joint. A selectively flexible connection/hinge connects the support portions at or near the joint such that rotation of the hinge provides for motion around the joint. Hinges used in these orthoses provide for rotation in a single plane. Transducers can provide for measurements of strain within the support and/or the position of the hinge. A microprocessor based control unit provides for monitoring of the measurements of the transducers. To the extent that previous instrumented orthoses have extended to multiple joints such as a knee brace extending to the foot, the measurements at the second joint have not involved rotation of the second joint. In other words, a force detector at the foot measures the force applied against the leg as a whole and not the force due to torque at the ankle. Further description of previous instrumented orthoses is found in U.S. Pat. No. 5,484,389 to Stark et al, entitled "Instrumented Orthopedic Restraining Device and Method of Use," incorporated herein by reference.

Various features of instrumented rehabilitation orthoses have been refined generally to provide for improved performance of the orthosis. Many of these features can be adapted for use in the improved orthoses described herein. These features are described in detail in copending and commonly assigned U.S. Provisional Application Ser. No. 60/098,779 to Stark et al., entitled "ORTHOSES FOR JOINT REHABILITATION," incorporated herein by reference, hereinafter "application 60/098,779". Certain of these features are described with particularity below, as appropriate. While application 60/098,779 is incorporated herein in its entirety, it is referred to for particular features in additional citations below.

Improved orthoses described herein provide for more sophisticated rehabilitation procedures than previous instrumented orthoses. Referring to FIG. 1, certain embodiments of an improved orthosis 100 include a first support portion 102, a second support portion 104, and a third support portion 106 such that multiple joints can be supported by orthosis 100. First support portion 102 preferably is connected to second support portion 104 by flexible connection/hinge 108. Similarly, second support portion 104 preferably is connected to third support portion 106 by flexible connection/hinge 110. Control unit/controller 112 can be connected to position sensors, described further below within hinges 108 and 110 and to strain gauges 114, 116. Alternative embodiments can include only one hinge or more than two hinges, with a correspondingly appropriate number of support portions.

Support portions 102, 104, 106 can be connected directly to hinges 108, 110 or by way of linkers 118, 120, 122, 124. In particular, linker 118 links support portion 102 with hinge 108, linker 120 links support portion 104 with hinge 108, linker 122 links support portion 104 with hinge 110 and linker 124 links support portion 106 with hinge 110. Linkers 118, 120, 122, 124 can have any desired rigid structure that is suitable given the structure of the support portion and the hinge.

Other embodiments 130 of the improved orthoses include hinges that provide for the motion of a joint in multiple planes. Referring to FIG. 2, first support portion 132 and second support portion 134 are connected to multidimensional hinge 136. As described further below, multidimensional hinge 136 can include a plurality of single plane hinges or more complex structures. Support portions 132, 134 can be directly attached to multidimensional hinge 136 or by way of linkers 138, 140, respectively. Orthosis 130 preferably includes, at least, one strain gauge 142 to measure forces applied at hinge 136.

A variety of constructions can be used for the support portions 102, 104, 106, 132, 134 (FIGS. 1 and 2) such that a support portion properly supports the respective body portion. Referring to FIG. 3, a first embodiment 150 of a support portion has frame members 152 and 154 that extend on either side of a body portion. Straps 156 extend from one frame member 152, 154 to the other to hold support portion 150 in place around the corresponding body portion. Straps 156 can be replaced with fabric sheets or other flexible or rigid connectors. Straps 156 can be secured to frame members 152, 154 with any of a variety of fasteners, such as snaps, buckles, clamps and hook and loop fasteners. The length of straps 156 can be adjusted using conventional designs. A rope and pulley system can be used for tightening and loosening support structure 150, as described further in application 60/098,779. Frame members 152, 154 connect directly to hinge elements 158, 160, although linkers can be used, if desired.

Referring to FIG. 4, an alternative embodiment 166 of a support structure that surrounds the corresponding body portion. Support portion 166 generally is somewhat rigid and can be constructed from a variety of materials. Preferred materials for the construction of support portion 166 include, for example, molded plastic shells, plaster, water-activated fiberglass, heat moldable thermoplastics, heat shrink plastic, and other cast forming materials. Support portion 166 can be premolded in various sizes such that a particular size is selected "off-the-shelf" based on measurements of the patient. Alternatively, support portion 166 can be constructed to provide a custom fit for a particular patient. These custom molded support portions are molded to fit the body portions of the particular patient by a trained physician or technician.

Whether or not a linker is used to connect a particular support portion and a hinge, a hinge can involve just one or a plurality of distinct hinge elements, as appropriate. As used herein, a hinge element is a physically distinct structure that has two or more lever arms that rotate relative to each other. A hinge includes one hinge element if a support portion has a single lever arm connecting it by way of the hinge to the other support portion and more than one hinge element if a support portion has multiple lever arms at distinct locations of attachment to the support portion.

For example, as shown in FIG. 2, hinge 136 has a single hinge element, which corresponds to the hinge itself. In contrast, in FIG. 3 the hinge includes two hinge elements 158, 160. Similarly, in FIG. 1 each hinge 108, 110 is depicted with two hinge elements. More than two hinge elements can be included in a single hinge, although it is preferably to use one or two hinge elements per hinge. Support structure 166 in FIG. 4 can be attached to one hinge element or two hinge elements by direct attachment or using appropriate linkers. The hinge elements are placed such that the joint can rotate when the orthosis is properly placed around the joint and the hinge elements are not in a locked position.

When forces are applied by the patient against the orthosis, the orthosis tends to change position relative to the patient's joint. This shifting reduces the effectiveness of any exercises being performed with the orthosis and may necessitate realignment of the orthosis for proper fit. The orthosis can be designed to reduce or eliminate this shifting.

A first approach to prevent a knee orthosis from slipping during exercise is to construct the orthosis with indentations in the femur supracondylar area just above the knee. An alternative solution involves the use of additional securing cuffs. Securing cuffs are designed to be tightened more during exercise routines to help secure the orthosis relative to the joint. Securing cuffs include a gripping element and, for example, can be placed against the leg above the knee such that when tightened, the gripping element applies pressure above the kneecap and pushes on the knee without pushing on the vasculature and lymphatic drainage posteriorly. In other embodiments, the securing cuffs can be appropriately placed. Cuffs 270, 272 can be tightened with a variety of fasteners including hook and loop fasteners.

Another approach to securing the orthosis involves securing the orthosis to a belt by way of one or more straps. Still another approach involves reducing the friction of the surface contacting the orthosis or part of the orthosis, for example, using a high friction, polymer sleeve. Still another approach to securing the orthosis involves the placement of crossed straps behind the joint. The straps apply forces that tend to maintain the straps in the fold of the joint. Furthermore, for a knee orthosis, the orthosis can end with a heel cup or other support placed along the bottom of the foot. Such a foot support preferably includes a strap or the like around the foot to hold the bottom of the orthosis at the bottom of the foot and, thus, to fix the hinge roughly at the knee.

With any of these approaches for inhibiting orthosis motion during use, the method preferably distributes the restraining forces sufficiently such that no portion of the skin is subject to excessive pressures that could bruise the skin as well as damage or interfere with neural or circulatory functions. Most of these approaches for preventing movement of the support portions are described further in the 60/098,779 application.

Hinges 108, 110, 136 (FIGS. 1 and 2) are intended to be interpreted broadly as any flexible connection that provides for angular motion of one support portion relative to another support portion. Hinges 108, 110, 136 preferably can be locked at a selected angle to protect the joint from undesired motion and/or to provide for isometric exercises. Hinges 108, 110 can be mechanical, electromechanical or a combination thereof, as described further below. In preferred embodiments, the hinge/flexible connection includes a position sensor such that the relative orientation of the hinge can be measured and monitored by the controller 112. For example, U.S. Pat. No. 5,052,375, to Stark et al. entitled "Instrumented Orthopedic Restraining Device and Method of Use," incorporated herein by reference, discloses the use of a potentiometer-like mechanism used as a position sensor. Other suitable position sensors can be used, such as magnetic or optical sensors that are either digital or analog devices. Position sensing is useful for the evaluation of range-of-motion exercises and a variety of other exercises, as described further in the 60/098,779 application.

Figure 6:
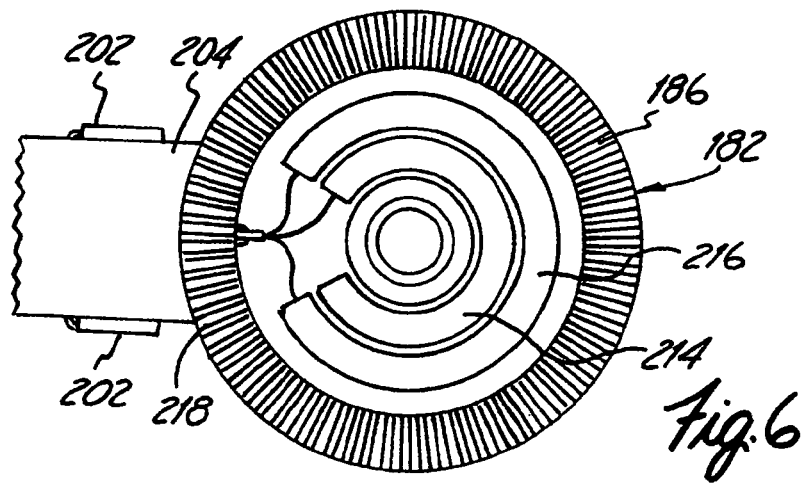
FIG. 6 is a side view of a portion of the hinge of FIG. 5 with another portion removed.

An embodiment of a suitable mechanical hinge capable of locking and unlocking is shown in FIG. 5. Hinge 180 includes a first engaging member 182 and a second engaging member 184. Members 182, 184 have teeth 186, 188, respectively, that engage when hinge 180 is in a locked position. Knob 190 is used to rotate bolt 192. Second engaging member 184 includes a threaded screw hole 194 that is mated with bolt 192 such that rotation of knob 190 moves knob 190 relative to member 184. Spring 196 tends to separate members 182, 184 from each other to the extent allowed by the relative position of bolt 192 within threaded hole 194. Clip 198 within recess 200 prevents separation of bolt 192 from member 184. Referring to FIG. 6, strain gauges 202 are located on frame 204. Frame 204 can be a linker between hinge 180 and a support portion or a component of a support portion.

Referring to FIGS. 5 and 6, hinge 180 includes a position sensing device in the form of a variable resister. In particular, member 184 includes two flexible wiper arms 210, 212. Wiper arms 210, 212 are in electrical contact with each other such that current can flow between them. Flexible wiper arm 210 contacts resistance element 214, while flexible wiper arm 212 contacts conducting element 216. Resistance element 214 and conducting element 216 have an electrical potential difference between them. Resistance element 214 has an electrical connection 218 at one end such that the electrical resistance resulting from current flow through resistance element 214 depends on the position of wiper arm 212 as determined by the relative angular orientation of member 184 relative to member 182. Wires 220 provide for electrical connection of resistance element 214 and conducting element 216 directly or indirectly to controller 112.

Figure 7:
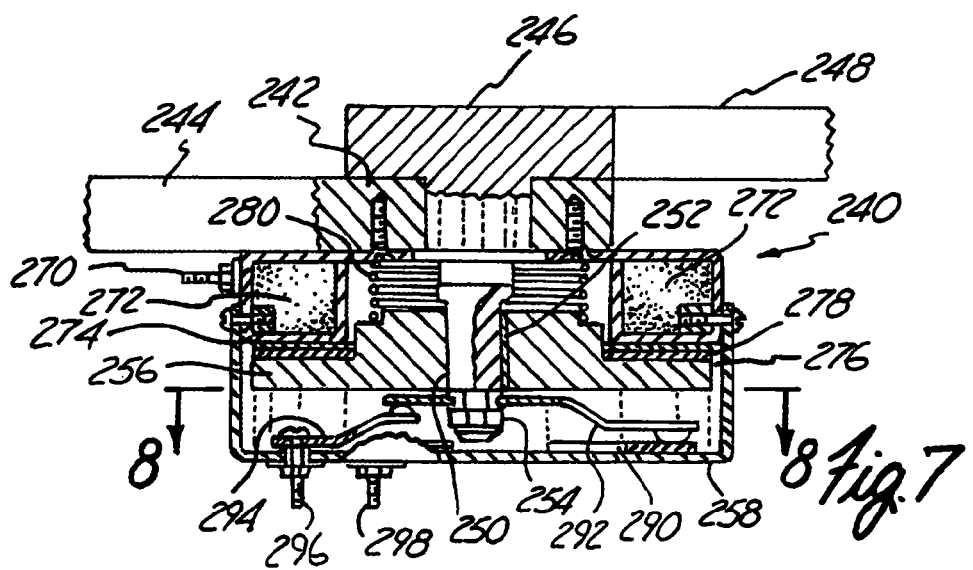
FIG. 7 is a top view of an electromechanical hinge, where a portion of the casing and other structures are removed to expose internal structure.

Referring to FIG. 7, an electromechanical hinge 240 is shown. Hinge 240 includes a first element 242, which connects to a first support portion 244, and a second element 246, which connect to a second support portion 248. Second element 246 connects with axle 250, which rotates within shaft 252 such that second element 246 can rotate relative to first element 242. Axle 250 is secured with nut 254. Shaft 252 passes through armature 256. Armature 256 is held within case 258. Case 258 is secured to first element 242.

Lead 270 electrically connects stator coil 272 within stator housing 274 with a current source. Stator coil 272 is designed to attract armature 256 when sufficient magnetic field is generated by electric current flowing through stator coil 272. The current can be supplied from controller 112. When armature 256 is attracted to stator coil 272, a pair of free riding discs 276, 278 are gripped between armature 256 and stator housing 274. Outer disc 276 is made preferably from a suitable metal, and inner disc 278 is made preferably from a suitable polymeric material to provide for a smooth grip between the surfaces and to prevent wear between the surfaces. A spring 280 biases armature 256 away from stator housing 274 when the magnetic attraction between coil 272 and armature 256 is insufficient to overcome the forces of spring 280. Sufficient attraction between coil 272 and armature 256 locks first element 242 relative to second element 246.

In preferred embodiments, a hinge provides selectable resistance to rotation for the performance of isotonic exercises. For example in the embodiment of FIG. 7, lesser amounts of attraction between coil 272 and armature 256 can result in selectable amounts of resistance/friction in the rotation of first element 242 relative to second element 246. The selectable resistance can be adjusted with controller 102 by varying the current supplied by controller 102 to stator coil 272.

Referring to FIGS. 7 and 8, a position sensor/variable resistor includes a resistance element 290 and wirer arm 292. Resistance element 290 is connected to case 258. Wiper arm 292 is keyed to rotate with axle 250 such that rotation of second element 246 relative to first element 242 rotates wiper arm 292 to different angular positions along resistance element 290. Conductor arm 294 provides current to wiper arm 292. Conductor arm is electrically insulated relative to case 258 while providing electrical connection by way of connection 296. Resistance element 290 is connected to electrical connection 298. Resistance measurements can be made by way of connectors 296, 298. Resistance measurements are a function of the angular position of support portion 244 relative to second support portion 248.

Mechanical and electromechanical hinges are described further in U.S. Pat. No. 5,484,389 to Stark et al., incorporated herein by reference. In particular, a suitable electromechanical hinge with variable resistance controllable by way of controller 112 is described further in published PCT application WO 96/36278, entitled "An Orthopedic Device Supporting Two or More Treatment Systems and Associated Methods," incorporated herein by reference.

A preferred embodiment of a left, mechanical hinge 300 is shown in FIG. 9. This hinge has a construction that provides for particularly easy release of the lock by a patient with one hand. The orientation of the hinge is measured by a position sensor to assist the patient in resetting the lock at a desired orientation. A right hinge would be the mirror image of the hinge in FIG. 9.

Hinge 300 includes a outer plate 302, washer 304, locking unit 306, ring lever 308, electrical resistance disc 310 and inner plate 312. Outer plate 302 is connected to a frame member 318. Strain gauge 319 can be attached to frame member 318. Outer plate 302 and inner plate 312 include concentric stop holes 320, bolt holes 322, connection holes 324 and slot 326. The corresponding holes are aligned between left outer plate 302 and inner plate 312.

One or two stop pins can be placed through two aligned stop holes 320 in outer plate 302 and inner plate 312 to define limits of hinge rotation. Bolts or other fasteners are secured through bolt holes 322 to hold hinge 300 together. Electrical resistance disc 310 rests within a hollow 338 within inner plate 312. Electrical resistance disc 310 makes electrical contact with wire 340.

Locking unit 306 includes control disc 346, slider 348, slider spring 350 and lock-out latch 352. Control disc 346 includes bolt holes 322 and a slit 354 in which slider 348 slides. Slider 348 has a groove 356 and an indentation 358 with a catch 360. Lock-out latch 352 has a knob 362 and a bar 364. Bar 364 slides within slots 326 and can fit within groove 356 to hold slider 348 in a depressed, unlocked, position.

Ring lever 308 is connected with a frame member 370. Ring lever 308 has an opening 372 with a diameter slightly larger than the diameter of control disc 346 such that control disc 346 can fit within opening 372. Control disc 346 preferably has a thickness slightly larger than ring lever 308. A set of concentric, notches 374 are located around the edge of opening 372 of ring lever 308. Catch 360 of slider 348 fits within the notches 374 to lock the hinge at a particular orientation when slider 348 is in an extended position. Depressing slider 348 against the force of spring 350 disengages catch 360 from one of the notches 374 such that hinge 300 is free to rotate within the bounds establishes by any stop pins. Ring lever 308 includes an electrical contact 376 set within a hole 378 that contacts electrical resistance disc 310. Electrical contact 476 is connected by wire 380 to controller 112 or alternative resistance meter.

Outer plate 302, inner plate 312, ring lever 308, control ring 346, lock-out latch 352 and slider 348 preferably are made from rigid, durable materials. In particular, outer plate 302 and inner plate 312 are preferably made from an aluminum alloy, and ring lever 308, control ring 346, lock-out slide 352 and slider 348 preferably are made from stainless steel. Spring 350 generally would be made from resilient steel or the like. Washer 304 and stop pin 330 generally are made from polytetrafluoroethylene or the like. Electrical resistance disc 310 can be made from circuit board material with a resistance element screen-printed on its surface.

Frame members 318 and 370 extend from hinge 300 such that movement of frame member 318 relative to frame member 370 involves rotation of hinge 300. When hinge 300 rotates, outer ring 302 and inner ring 312 rotate relative to ring lever 308. Outer ring 302, inner ring 312 and control disc 346 are held fixed with respect to each other by way of bolts passing through bolt holes 322. The orientation of hinge 300 is locked unless slider 348 is depressed such that catch 360 is withdrawn from notches 372. Lock-out slide 352 can hold slider 348 in the depressed, unlocked position. The position of ring lever 308 relative to inner ring 312 can be measured by way of the position of electrical contact 376 along electrical resistance disc 310. The relative position of electrical contact 376 along electrical resistance disc 310 provides a variable electrical resistance useful for position/orientation sensing.

It may be convenient to provide for release of a hinge with a remote control. The release of an electromechanical hinge using a command from the controller is described above. It may be desirable to have a simple mechanical remote release. A simple photographic shutter release can be adapted for this purpose with the hinge of FIG. 9. The shutter release can be screwed at its threaded tip into hinge 300 at threaded hole 394 in control ring 346. Pressing the plunger of the cable release advances a cable, which in turn depresses slider 348 thereby unlocking hinge 300. Alternative designs for mounting of a manual hinge release involve pulling a plunger that in turn pulls slider 348 such that the lock is disengaged and such that releasing the plunger reestablishes the hinge lock.

While electronic control of the resistance in a flexible connection/hinge has advantages, cost and design simplicity favors a purely mechanical hinge. Referring to FIG. 10, With a purely mechanical hinge, such as shown in FIG. 5, strain gauge readings can be accurately calibrated to reflect the forces applied to move the hinge against a setting on a mechanical resistance applicator. Thus, control unit 112 can be used to monitor the isotonic exercises even though the resistance is not electronically controlled. A mechanical resistance applicator can be made integral with the hinge, but in preferred embodiments the resistance unit can be separated from the hinge such that no resistance is applied to the hinge when resistance is not desired. A resistance applicator can designed to amplify small changes in the resistance that correlate with easily made changes in the position of a knob.

Referring to FIG. 10, a cross section through the center of an embodiment of resistance applicator 400 is shown. Resistance applicator 400 includes housing 404, a crank 406, a compression structure 408, knob 410, bearing unit 412, washer 414 and spacers 416.

Housing 404 includes lock pins 428. A second lock pin is not shown in the sectional drawing. Lock pins 328 provide releasable connection for attachment of resistance applicator 400 to a hinge, such as hinge 300 of FIG. 9. In particular, lock pins 428 of resistance applicator 400 can be secured through connection holes 324 to releasably secure resistance applicator 400 in an operable position with respect to hinge 300. Alternative locking approaches can be used for the attachment of the friction applicator to the hinge. Housing 404 includes threaded hole 432 for engaging knob 410. Housing 404 further includes cylindrical protrusion-438 for engaging compression structure 408.

Crank 406 includes cylindrical extension 454' for engaging compression structure 408 and pads 458, which engage a support portion, such that rotation of the hinge of the orthosis rotates crank 406 relative to housing 404.

Compression structure 408 provides for small changes in the resistance due to changes in the distance between washer 414 and housing 404 as knob 410 is rotated, thus amplifying resistance changes by way of the knob. Compression structure 408 generally produces friction as a result of shear forces within compression structure 408 due to relative motion of housing 404 and crank 406. In one embodiment, compression structure 408 includes alternating crank discs and housing discs to form a multiple clutch plate. Crank discs engage crank 406, such that the crank discs rotate with crank 406. Housing discs have a central hole shaped to engage protrusion 438 in housing 404, such that housing discs rotate with housing 404.

Knob 310 includes a threaded shaft 482 with threads and diameter suitable for engaging the threads of threaded hole 432 in housing 404. Bearing unit 412 preferably includes a ring of ball bearings in a bearing case. Bearing unit 412 can be replaced with other bearing structures or other friction reducing approaches such as hydro bearings.

Washer 414 has a suitable inner diameter such that threaded shaft 482 can pass through the inner diameter but bearing unit 412 cannot pass. Washer 414 has an outer diameter such that washer 414 rests on extension 454 of crank 406 covering the opening to compression unit 408 between housing 404 and crank 406. Two optional spacers preferably are located with one on each side of compression unit 408. The spacers have the shape of a washer but with a suitably larger inner diameter and smaller outer diameter than washer 414 such that the spacers fit within the cavity between crank 406 and housing 404.

The primary components of the resistance applicator 400 preferably are made from metals and/or alloys. Aluminum alloys and stainless steel are suitable metals for the construction of housing and crank components. Rigid polymers can be used in place of metals for the housing and crank elements. The spacers preferably are made of brass. The housing disc preferably is made from spring steel, and the crank disc preferably is made from spring tempered phosphor bronze. The bearing case can be made from Nylon®.

Resistance applicator 400 is designed to attach to a hinge such that housing 404 moves with a frame member attached to one side of the hinge while crank 406 moves with a frame member attached to the other side of the hinge. Thus, rotation of the hinge results in rotation of housing 404 relative to crank 406. Tightening of knob 410 presses washer 414 down onto compression unit 408. Housing rings and crank rings rotate relative to each other when housing 404 moves relative to crank 406. Increasing the pressure on compression unit 408 results in increased resistance in the rotation of housing 404 relative to crank 406 because of friction between housing rings and crank rings. This design provides for sensitive adjustment rotational resistance by rotation of knob 410. The improved hinge 300 shown in FIG. 9 combined with the improved resistance applicator 400 is described further in the 60/098,779 application.

In alternative embodiments, a hinge takes the form of an articulating hinge 490, as shown in FIG. 11. Articulating hinge 490 can be made with resilient collapsible materials such as a bendable straw, sliding sections that can slide past each other to articulate, or other similar constructions. Sliding sections can be locked relative to one another by way of clamps 492 attached to slots 494 defining a range of motion, where the clamps are tightened manually with wing nuts or the like, or electronically with solenoids or the like. As shown in FIG. 11, articulating hinge 490 is connected to two support portions 166 that surround the corresponding body portions. Alternatively, one or both support portions 166 can be replaced with other types of support portions or by linkers that connect the support portions to hinge 490.

Certain joints such as the knee are cams that do not involve rotation about a single axis. A biaxial hinge can be used to more closely approximate the motion of the joint cam. A biaxial hinge 500 generalizing on the structure of hinge 300 is shown in FIG. 9. Biaxial hinge 500 includes a proximal arm 502 and a distal arm 504. Proximal arm 502 includes teeth, which engage teeth on distal arm 504. Proximal arm 502 further includes lock notches and an electrical contact for position (orientation) sensing. A control ring operates similarly to control ring 346 in hinge 300 to control the locking/unlocking of the hinge. Further details on biaxial hinge 500 can be found in the 60/098,779 application.

Orthosis 130 shown in FIG. 2 includes hinge 136 capable of rotation in multiple planes to provide for multiple ranges of motion about a single joint. A first embodiment of a hinge capable of motion in multiple planes is shown in FIG. 13 and an exploded view in FIG. 14. Hinge 510 includes rod 512 that moves within sleeve 514. Sleeve 514 has four resilient sections 516 that form a truncated conical shape. Sleeve 514 further has threads 518. Cap 520 fits over and screws onto sleeve 514. Cap 520 includes worm gear threads 522. Lever 524 has mated worm gear threads 526 to complete the worm gear with lever 524 adjacent cap 520.

Cap 520 can be screwed to varying degrees to increase or decrease the tension at resilient sections 516. Tension at resilient sections 516 grips rod 512 to a corresponding degree. The worm gear comprising threads 522 and 526 can be used to screw cap 520 on to or off from sleeve 514. The worm gear is advanced by the rotation of lever 524.

Hinge 510 moves in two degrees of freedom, with one degree of freedom corresponding to the rod 512 moving into or out from sleeve 514. The rotation of rod 512 provides motion in the second degree of freedom. Screwing cap 520 sufficiently locks both degrees of freedom. Hinge 510 can be incorporated into a shoulder orthosis such that motion of the rod 512 into and out from sleeve 514 provides for movement of the patient's elbow toward or away from the torso while rotation of rod 514 provides for movement of the arm toward the front or toward the rear.

In preferred embodiments, hinge 510 includes position sensors such that the orientation in each degree of freedom can be measured. In one embodiment, rod 512 includes a resistive element 530 that can be used to contact a conductive brush within sleeve 514. Resistive element 530 can be used to measure the position of rod 512 as it projects to varying degrees within shaft 512. Similarly, rod 512 can further include a conductive brush 532 that contacts a resistive element. Brush 512 can be used to measure the orientation of rod 512 depending on the rotation of rod 512 within sleeve 514.

A second multidimensional hinge 540 is displayed in FIG. 15. Hinge 540 includes a first hinge 542 attached to a first lever arm 544. A second lever arm 546 links first hinge 542 with second hinge 548. Rotation about the first hinge involves relative rotational motion of first lever arm 544 relative to second lever arm 546 and second hinge 548. Third lever arm 550 is attached to second hinge 548, such that rotation about second hinge 548 rotates second lever arm 546 relative to third lever arm 550.

Preferably, first hinge 542 and second hinge 548 are separately lockable, and, optionally, have adjustable resistance. Designs for single plane hinges described above can be used for first hinge 542 and second hinge 548. These hinges have position sensors, such that the orientation of each hinge can be measured. Multidimensional hinge 540 can be used advantageously in orthoses for joints that move in multiple planes.

For example, hinge 540 can be used in a shoulder brace where one of lever arms 544 and 550 moves with the patient's arm while the other is fixed to their abdomen.

Strain gauges 114, 116, 142 can be useful for the performance of both isometric and isotonic exercises. Strain gauges can be placed at any suitable location such that the strain in the underlying material reflects the torque applied between two respective flexibly connected body portions surrounding the joint of interest. Suitable locations for the strain gauges involve placement of the strain gauges on a structure that is attached to the corresponding hinge. The strain gauges generally are located on a rigid element near the hinge that is under stress when torque is applied to the hinge. Since different structures have different relationships between the support portions and the hinge, the preferred locations for the strain gauges depend on the particular construction of the orthosis.

Whether monitoring isometric exercises or isotonic exercises, strain measurements obtained by way of a strain gauge can be correlated with the corresponding forces applied by the patient. Strain gauges 114, 116 are connected to controller 112, which evaluates the strain based on the electrical properties of the strain gauge. Suitable strain gauges are available from Vishay Micromeasurements Group (Raleigh, N.C.) (e.g., type 125AD, part number EK-XX-125AD-350 with dual copper pads), or JP Technologies (San Bernardino, Calif.). Evaluation of the strain is discussed further below in the context of controller 112.

Figure 16:
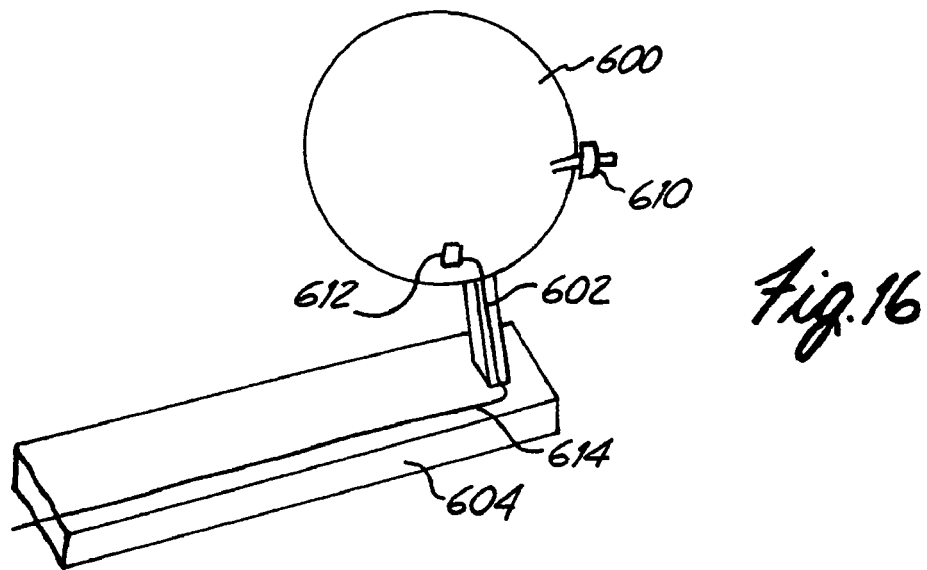
FIG. 16 is a fragmentary, perspective view of an orthosis with a squeeze ball for the patient's hand.

As noted above, for a variety of treatments, it is useful to incorporate an instrumented hand hold. Referring to FIG. 16, a hand hold 600 is mounted on top of a support 602. Support 602 projects from a arm rest 604. Support 602 should have a height for comfortable gripping of hand hold 600. In preferred embodiments, arm rest 604 forms part of an instrumented orthosis that, at least, extends past a patient's elbow. Arm rest 604 can be part of a shoulder brace, as described further below. Hand hold 600 can have any comfortable shape for gripping, such as spherical or cylindrical.

Figure 17:
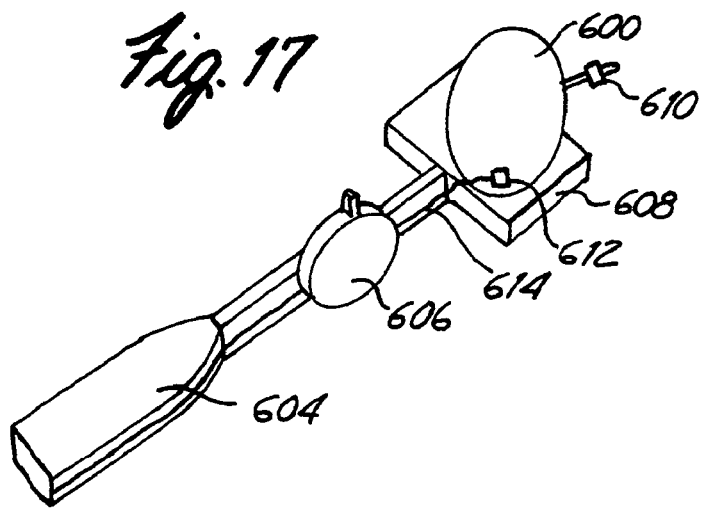
FIG. 17 is a fragmentary, perspective view of an orthosis with a squeeze ball of FIG. 16 and a wrist hinge.

As shown in FIG. 17, arm rest 604 can include a wrist hinge 606. Wrist hinge 606 preferably includes a position sensor, a position lock and adjustable friction, as described above with respect to preferred embodiments of various hinge designs. Hand hold 600 rests on a hand support 608 that connects to arm rest 604 through wrist hinge 606. As shown in FIG. 17, hand hold 600 rests on hand support 608 without elevation with a support 602.

Hand hold 600 can be a bladder filled with a fluid, such as a gas, liquid or a pseudo-liquid formed by a granular material or the like. Alternatively, hand hold 600 can be formed from a compressible material, such as a foam or the like. The degree of compressibility can be selected to obtain a suitable amount of exercise from hand hold 600. If hand hold 600 is filled with a fluid, hand hold 600 can include one or more valves 610. Valve 610 can be used to add or remove fluid from hand hold 600 to vary the nominal pressure in ball 600.

Hand hold 600 preferably includes a pressure sensor 612 or a strain gauge. Pressure sensor 612 can be used to measure the amount of force applied by a patient when squeezing hand hold 600. When hand hold 600 is squeezed, the pressure increases in hand hold 600, if hand hold 600 contains a fluid. A strain gauge measures forces applied to squeeze ball 600 according to the increased strain along the surface of ball 600. Pressure sensor 612 and/or a strain gauge generally are connected to controller 112 by wire 614.

Suitable strain gauges were described above. Pressure sensor 612 can be any reasonable type. A variety of suitable pressure sensors are commercially available. Preferred pressure sensors include the MPX series of pressure sensors manufactured by Motorola because of their linear output and small size, and NPP 301A from Lucas Novasensor, Fremont Calif., which are small and inexpensive. Other suitable pressure sensors use silver oxide ink surfaces separated by a dielectric material or piezoelectric materials that produce a voltage when stressed.

Figure 18:
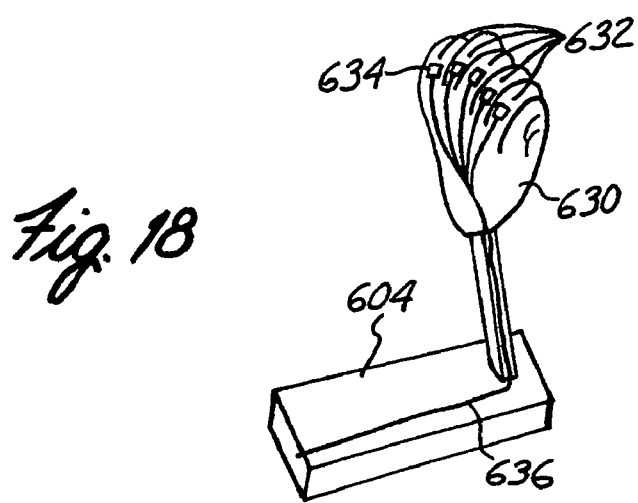
FIG. 18 is a fragmentary, perspective view of an orthosis with a hand grip.

In an alternative embodiment, the orthosis includes a hand grip 630, as shown in FIG. 18. Hand grip 630 can be mounted in the same way with respect to an arm support 604 as squeeze ball 600. Hand grip 630 includes finger rests 632. Finger rests 632 are indentations that provide a specific location for resting each finger. In preferred embodiments, hand grip 630 includes pressure sensors/strain gauges 634 in the vicinity of each finger rest 632. Pressure sensors/strain gauges 634 can be used to measure the force approximately corresponding to the force applied by a particular finger. Pressure sensors/strain gauges 634 are connected to controller 112 by way of wires 636.

Hand grip 630 generally includes some compartmentalization such that forces applied by one finger are approximately segregated in effect within a corresponding compartment. Thus, if hand grip 630 includes a fluid or fluids, the fluids can be placed within separate compartments for each finger, preferably separated by a relatively rigid barrier. Similarly, a compressible material, e.g., a foam, supporting each finger can be similarly separated by a relatively rigid barrier.

An instrumented orthosis can be configured to delivery one or more monitored, therapeutic energy treatments along with the capability of performing monitored exercise. The therapeutic energy is delivered by way of an energy transducer. Suitable types of energy transducers include, for example, ultrasonic transducers, pulsed electromagnetic field transducers, implantable electrical current transducers, surface electrical current transducers, and electrical muscle contraction stimulator. The transducers are located at an appropriate position to provide treatment for the injured area. The transducers preferably are controlled and monitored by controller 112. Further discussion of combined treatment approaches using exercise and/or energy propagating transducers are described in published PCT application WO 96/36278, entitled "An Orthopedic Device Supporting Two or More Treatment Systems and Associated Methods," incorporated herein by reference.

In simplified embodiments, controller 112 may just include analog circuits and a suitable display. In preferred embodiments, controller 112 includes a digital processor to provide a more sophisticated interface with the patient and/or with a health care professional, and to preform more involved monitoring functions. The digital processor preferably is a microprocessor. The digital processor can be programmed in any of a variety of computer languages including, for example, basic, assembler, C, C++ and the like. Preferably, controller 232 is portable, which in this context means that the controller is small enough to be ambulatory with the patient. More preferably, controller 112 is small enough to be held in the hand of a patient, and even more preferably to be placed in a standard shirt pocket.

A preferred microprocessor based controller 112 has several subsystems including a power supply such as a battery, a transducer bias circuit such as described below, A/D converters, a microprocessor, real time clock, RAM and non-volatile storage such as FLASH, SRAM or EEPROM, a graphic display such as a 64×128 pixel LCD display with a corresponding driver, keypad, audible or tactile feedback device, data link to transducer, and an integral modem or RS232 standard output for serial connection or modem access.

In one particular embodiment, the microprocessor is a Motorola MC68HC11A1FN 8-bit microcontroller with built-in deep sleep shutdown mode for power conservation between active events, a programmable serial interface and an 8-channel, 8-bit A/D converter. In this embodiment, controller 232 can provide analog multiplexing and A/D conversion for up to 8 analog input signals over a voltage range from 0.0 to +5.0 volts. For example, three of the channels can be devoted to provide signal conditioning for up to three strain gauges, and three of the channels can be devoted to providing signal conditioning for up to three position (angle) sensors. The remaining two input channels then can be used for additional treatment devices. If desired, added sensors can be handled by multiplexing and duty-cycling.

In this preferred embodiment, the controller module memory includes SRAM, FLASH and EEPROM, where each section is independently addressable. Each section can support, at least, 32K words with 8-bits (1 byte) per word. The EEPROM supports in-circuit reprogramming by way of the microcontroller serial channel for code updates. The FLASH memory provides non-volatile storage of recorded data. The real time clock is battery powered to allow time keeping to continue when the microcontroller circuitry is off. The real time clock is capable of generating periodic interrupts at a programmable rate to power switching circuitry to activate the microcontroller during an alert mode of operation.

The RS-232 interface consists of three conductor (TxD, RxD and GND) jack type connector with a mechanical switch to automatically switch power on to all on-board electronics when the plug is inserted. The baud rate of the interface is programmable with standard rates such as 9600 and 19200. A suitable display is a Densitron™ LE3328 LCD with Hitachi HD61202 and HD61203 LCD controller chip sets. The display can be run with a five volt supply that can be separate or not from the power supply for the rest of controller 232. In this embodiment, a three key keypad is interfaced with the microcontroller.

All of the components of controller 112 can be placed on the orthosis or in a separate case. The components of controller 112 can be integrated into a single package or physically partitioned into portions mounted on the orthosis frame and/or portions placed into one or more small cases.

Controller 112 preferably stores a software program that manages the use of the device for patient rehabilitation. The software can provide for alerting the patient to scheduled times for the performance of exercises using audible and/or vibratory signals. Controller 112 preferably provides instructions on the exercises as well as feedback and reinforcement messages to the patient. The software preferably is custom programmed for the patient by a health care professional based on an evaluation of the patient's condition. Approaches for programming the control unit is described further in the 60/098,779 application.

Stored information relating to the patient's performance of exercises generally is downloaded to the supervising health care professional at specified intervals. The download of the information can be performed in a variety of ways. If the patient goes to the office of the health care professional, controller 112 can be directly connected to the monitor station/computer using the RS232 port or other port using suitable protocols including standard protocols. Alternatively, controller 112 can be attached to a modem by way of the RS232 port or other suitable port. Since with certain embodiments the file sizes are relatively small, a single chip, 9 volt supply Rockwell® 2400 baud or 9600 baud modem can be used. Controller 112 can be in radio communication with a monitor station. Controller 112 then would include a radio transmitter and, optionally, a receiver. Radio communication with a monitor station is described further and U.S. Pat. No. 5,823,975 entitled "Local Monitoring System For an Instrumented Orthopedic Restraining Device and Methods Therefore," incorporated herein by reference. The display or a television set similarly can be in communication with controller 112 by way of radio transmissions or infrared communication such that a wire attachment is not necessary. Additional features of the controller are describe in the 60/098,779 application.

In order for the value of electrical resistance associated with a strain gauge to be useable as a measure of applied stress during isometric exercises, the values must be referenced to a "null" valve approximately corresponding to a value when no strain is applied to the orthosis. The null value can be set by a manual adjustment performed by the health care professional or by the patient. The "null" value, however, is preferably established automatically without the need for calibration by the user. Furthermore, the variations in the resistance due the strain gauge preferably are converted into a voltage value that is amplified to make efficient use of an analog-to-digital (A/D) converter with a specified number of binary digits. A preferred summing amplifier circuit for calibrated strain gauge measurement is described in detail in the 60/098,779 application.

Further aspects of the improved orthoses are illustrated by reference to three particular preferred embodiments.

A. Shoulder Brace

Figure 19:
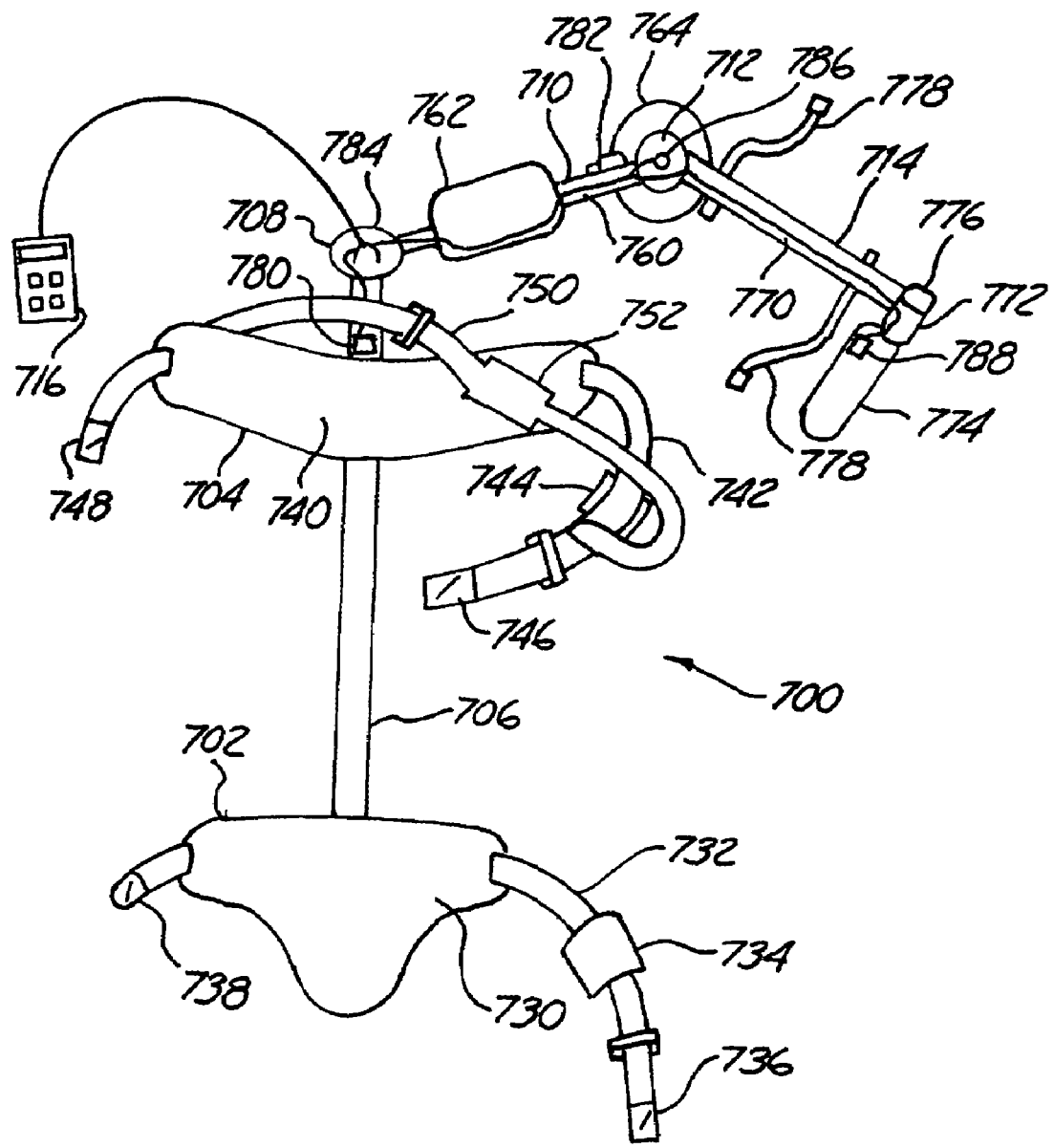
FIG. 19 is a front view of a shoulder orthosis.

Referring to FIG. 19, a preferred embodiment of a shoulder brace 700 includes trunk support 702, under arm support 704, upright support 706, shoulder, hinge 708, arm support 710, elbow hinge 712, fore arm extension 714 and controller 716. Trunk support 702 includes a padded hip rest 730 contoured to rest comfortably against a patient's hip and distribute any downward forces over a reasonable area. Padded hip rest 730 can include a relatively rigid shell, made from fiber glass, polytetrafluoroethylene other suitable polymers, metal or the like. Padding, such as cloth covered foam padding, can be placed adjacent the rigid shell. Trunk support 702 generally further includes a strap 732, which can wrap around a patient's waist to secure trunk support 702. Strap 732 preferably has an adjustable length, optional padding 734 and a fastener component 736, such as a portion of a hook-and-loop fastener, a buckle or any other suitable fastener component. A second fastener component 738 is attached to a strap or directly to padded hip rest 730, as desired. Second fastener component 738 is the complement to fastener component 736, such that fastener components 736, 738 can be secured to each other.

Under arm support 704 includes a padded support portion 740, which can include a relatively rigid shell with padding located along the inner and/or upper surface. Under arm support 704 further includes a strap 742, which can wrap around a patient's chest to secure under arm support 704. Strap 742 has an optional pad 744, and preferably has an adjustable length and a fastener component 746. A second fastener component 748 can be attached to another strap or directly to padded support portion 748. Fastener components 746, 748 can be complementary components of a buckle fastener, a look-and-loop fastener, or any other suitable fastener Under arm support 704 further includes a shoulder strap 750. Shoulder strap 750 can include padding 752, and preferably has an adjustable length. In this embodiment, shoulder strap 750 extends from strap 742 to padded support portion 740, although other configurations are possible. Shoulder strap 750 is designed to extend over the opposite shoulder of the patient relative to the shoulder supported by under arm support 704.

Upright support 706 connects padded hip rest 730, padded support portion 740, and shoulder hinge 708. Upright support can be constructed from any rigid material such as metal, fiber glass or other rigid material or materials. Upright support 706 can be bolted to padded hip rest 730 and padded support portion 740, molded into a rigid shell of padded hip rest 730 and padded support portion 740, or secured to padded hip rest 730 and padded support portion 740 in any other reasonable fashion. Upright support 706 can attach directly to a lever arm of shoulder hinge 708 or through a linking element connecting upright support 706 to a lever arm of shoulder hinge 708. Upright support 706 holds padded hip rest 730, padded support portion 740 and shoulder hinge 708 at constant relative positions.

Shoulder hinge 708 preferably is a hinge capable of motion in multiple planes. Suitable designs for hinges with releasable motion in multiple planes for use as shoulder hinge 708 are described above. As noted above, upright support 706 is attached to one lever arm of shoulder hinge 708. A second lever arm of shoulder hinge 708 is attached to arm support 710.

Arm support 710 preferably includes a support brace 760 and padded arm support 762. Support brace 760 is attached to a lever arm of should hinge 708 and to a lever arm of elbow hinge 712, either directly or through a linker. Padded arm support 762 is connected to support brace 760. Padded arm support helps the patient hold their arm in a proper position along support brace 760.

One lever arm of elbow hinge 712 is connected to support brace 760 and a second lever arm of elbow hinge 712 is connected to fore arm extension 714. Elbow hinge 712 is oriented such that rotation at the patient's elbow results in rotation of the hinge, if hinge 712 is in an unlocked setting and the patient's arm is properly located along arm support 710 and fore arm extension 714 with their hand gripping hand hold 774. Elbow pad 764 is attached to elbow hinge 712 or support brace 760. If desired, the lengths of arm support 710 and/or fore arm extension 714 can be adjustable.

Fore arm extension 714 includes extension shaft 770, bend 772 and hand hold 774. Shaft 770 can be made adjustable, such that the distance from the elbow to the hand can be set to an appropriate value. Bend 772 connects shaft 770 with hand hold 774. Hand hold 774 preferably is a padded grip. Bend 772 preferably is connected to shaft 770 by way of a wrist hinge 776. Fore arm extension 714 preferably include straps 778 to secure the patient's arm. The hinge shown in FIG. 9 can be adapted for use as elbow hinge 712 and wrist hinge 776.

Shoulder brace 700 preferably includes a plurality of transducers. As depicted in FIG. 19, strain gauges 780, 782 are associated with upright support 706 and support brace 760, respectively. Strain gauges 780, 782 can supply measurements related to forces applied against a locked hinge or forces applied for rotation of shoulder hinge 708 and/or elbow hinge 712. Shoulder hinge 708 preferably includes a multi-dimensional position sensor 784, as described above. Elbow hinge 712 preferably includes a position sensor, 786. Furthermore, hand hold 774 can include one or more pressure/stress transducers 788, to provide measurements related to forces applied by the patient's hand.

The transducers are preferably connected to controller 716, generally by wires, although transmitter based approaches can be used. Suitable designs for controller 716 were described above with respect to controller 112 of FIG. 1. Straightforward modifications can be made to accommodate all of the transducers desired for shoulder brace 700.

To use shoulder orthosis 700, a patient can slip shoulder strap 750 over their arm and head. With the weight of shoulder brace supported on shoulder strap 750, straps 732 and 742 can be secured to distribute the weight and balance of shoulder brace 700 over the various support segments. With brace 700 secured to the patient's torso, the patient can position their arm along arm support 710 with their appropriate hand gripping hand hold 774. Shoulder brace 700 can serve as a support for the patient's back, shoulder, elbow, wrist and/or hand. Furthermore, shoulder brace provides for a variety of exercises to assist with the recovery of an upper body injury, and/or to prevent the deterioration from lack of use of joints near an injury. Potential exercise programs are described further below.

B. Lower Extremity Full Leg Brace

Figure 20:
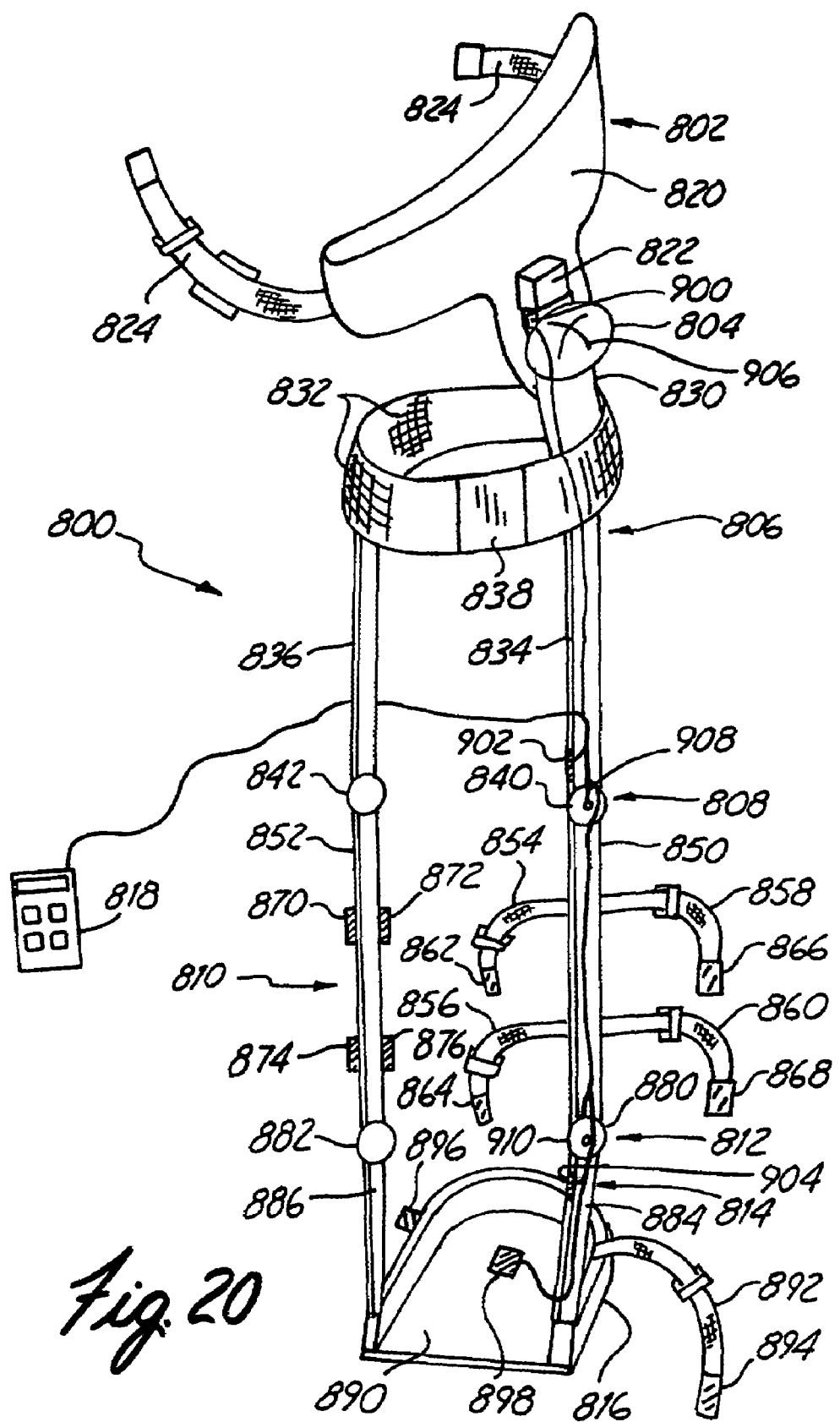
FIG. 20 is a perspective, front view of a lower extremity orthosis.

Referring to FIG. 20, a particular embodiment of a full leg brace 800 includes waist support 802, hip hinge 804, thigh support 806, knee hinge 808, shin support 810, ankle hinge 812, ankle/foot support 814, foot rest 816 and controller 818. Waist support 802 preferably secures at the patient's waist to support the upper portion of full leg brace 800. Waist support 802 can have a similar design as trunk support 702, described above. Waist support 802 generally includes support section 820 and hinge link 822. Support section 820 can be formed from one or more segments of rigid shell with inner padding to cushion contact with the patient. Multiple rigid shell segments can be connected with flexible segments for easier fastening around the patient's waist. Waist support includes straps 824 or the like to provide for easy fastening and unfastening of waist support 802. Hinge link 822 provides for rigid connection of support section 820 with hip hinge 804.

Hip hinge 804 preferably is a hinge capable of motion in multiple planes. Suitable instrumented hinges with motion in multiple planes were described above. Preferred hip hinges 804 provide for motion of the leg forward-to-back as well as side-to-side, when the hinge is unlocked.

Thigh support 806 includes a hinge link 830, a support segment 832 and frame members 834, 836. Hinge link 830 provides rigid support between hip hinge 804 and support segment 832. Support segment 832 preferably encircles the patient's thigh, to secure thigh support 806. Support segment 832 generally includes rigid shell segments with padding. In preferred embodiments, support segment 832 includes flexible segments connecting rigid shell segments. One or more flexible segments preferably include a releasable fastener 838, such as a hook-and-loop fastener to provide for easy fastening and unfastening of support segment 832. Framemembers 834, 836 provide rigid connection between support segment 832 and knee hinge 808. Frame members 834, 836 can be designed to have adjustable lengths to provide a proper fit.

In this embodiment, knee hinge 808 includes hinge elements 840, 842, connected, respectively, to frame members 834, 836. Several suitable designs for instrumented hinge elements 840, 842 are described above. Hinge elements 840, 842 connect to shin support 810, such that shin support 810 and thigh support 806 connect to different lever arms of each hinge element 840, 842.

Shin support 810 includes frame elements 850, 852 and straps 854, 856, 858, 860 connected to frame element 850. Frame elements 850, 852 connect with hinge elements 840, 842, respectively. The patient's leg rests between frame elements 850, 852. Straps 854, 856 connect over the front of the patient's leg, while straps 858, 860 connect behind the patient's leg. Straps 854, 856, 858, 860 can include padded portions. Straps 854, 856, 858, 860 generally have an adjustable length and include fastener element 862, 864, 866, 868. Matched fastener elements 870, 872, 874, 876 are connected to frame element 852 directly or with straps. Fastener elements 870, 872, 874, 876 can be elements of a clip, a buckle, hook-and-loop fastener or other suitable fastener. Fastener elements 870, 872 and 874, 876 together can be single sheets of hook or loop material of a hook-and-loop fastener.

In this embodiment, ankle hinge 812 includes hinge elements 880, 882, connected respectively to frame elements 850, 852. Several suitable designs for instrumented hinge elements 880, 882 are described above. Hinge elements 880, 882 connect to ankle/foot support 814, such that ankle/foot support 814 and shin support 810 connect to different lever arms of each hinge element 880, 882.

Ankle/foot support 814 includes frame segments 884, 886. Frame segments 884, 886 connect with hinge elements 880, 882, respectively. Frame segments 884, 886 further connect with foot rest 816. Frame segments can be made adjustable such that the distance from hinge elements 880, 882 to foot rest 816 can be adjusted to the proper length for the patient.

Foot rest 816 includes a heel support 890 and foot strap 892. Heel support 890 is contoured to the fit the rear portion of a patient's foot. Foot strap 892 wraps around the patient's foot to secure the patient's foot against heel support 890. Strap 892 preferably has an adjustable length to obtain a proper fit. Foot strap 892 includes a fastener portion 894 that connects with mated fastener portion 896. Fastener portion 896 generally is connected to heel support 890 on the opposite side relative to the connecting point of foot strap 892. Fastener portions 894, 896 can be portions of any suitable fastener, such as buckles, clasps, hook-and-loop fasteners and the like.

Full leg brace 800 preferably includes a plurality of transducers. As depicted in FIG. 20, strain gauge 900 is associated with hinge link 822. Strain gauge 902 is associated with frame member 834. Strain gauge 904 is associated with frame segment 884. Strain gauges 900, 902 and 904 can supply measurements related to forces applied against a locked hinge or related to rotation of hip hinge 804, knee hinge 808, and/or ankle hinge 812. Hip hinge 804 preferably includes a multi-dimensional position sensor 906, as described above. Hinge element 840 of knee hinge 808 preferably includes a position sensor, 908, to measure the orientation of knee hinge 808. Similarly, hinge element 880 of ankle hinge 812 preferably includes a position sensor, 910. Furthermore, heel support 890 can include one or more pressure/stress transducers 898, to provide measurements related to forces applied by the patient on their heel.

The transducers are preferably connected to controller 818, generally by wires, although transmitter based approaches can be used. Suitable designs for controller 818 were described above with respect to controller 112 of FIG. 1. Straightforward modifications can be made to accommodate all of the transducers desired for full leg brace 800.

The brace shown in FIG. 20 is intended to be worn on the patient's left leg. A corresponding brace can be constructed for the patient's right leg based on this design by connecting the leg portion of the brace to the other side of waste support section 820. The leg portion can be identical in construction to the left leg version shown in FIG. 20, or the leg portion can involve reversal of the left and right hand elements on the leg portion, such that the resulting right leg portion corresponds to the left leg portion reflected through a symmetry plane going through the center of the leg portion. Furthermore, a lower extremity brace that supports both of the patient's legs can be constructed with a single waste support section 820 connected through two hip hinges 804 to appropriate supports for both legs.

For use, full leg brace 800 is placed around the patient's leg with the foot supported by foot support 816, with waist support 802 secured at the patient's waist, and support segment 832 secured around the patient's thigh. Straps 854, 856, 858, 860 and 892 are appropriately fastened to fully support full leg brace 800. Full leg brace 800 can be used to provide valuable support for the patient as well as for the performance of a variety of monitored, programmed exercises, as described further below.

C. Stroke Brace

Preferred embodiments of a stroke brace have upper body and lower extremity support. For the most common stroke debilitation, i.e., hemiparesis affecting one whole side of the body, the shoulder brace and full leg brace described above can be combined. Shoulder orthosis 700 of FIG. 19 can be used along with lower extremities orthosis 800 of FIG. 20. In these embodiments, a common trunk support is substituted for trunk support 702 and waist support 802. The common trunk support is straightforward to design by incorporating the features of trunk support 702 and waist support 802.

With respect to instrumentation, transducers from orthoses 700, 800 can be connected to separate controllers 716, 818, or the transducers preferably can be connected to a single controller adapted to accommodate all of the transducers of both orthoses. Shoulder orthosis 700 can be physically connected to lower extremities orthosis 800 for stability, or orthoses 700, 800 can be physically disconnected except for possibly connection to a single controller.

2. Rehabilitation Using Orthoses

The controllers described above preferably are programmed under the supervision of an appropriate health care professional. In one preferred embodiment, the controller has four modes of operation: OFF, STANDBY, ALERT and FULL ON. In the OFF mode, primary and backup battery power are removed, and no operations are taking place in the controller. In the STANDBY mode, no primary battery power is online, and backup battery power is used to maintain the real time clock and SRAM. Back-up power can be supplied by a coin cell or the like. STANDBY mode is generally used while the primary battery is being replaced or recharged.

In ALERT mode, the real time clock produces a signal at programmed, periodic intervals to activate all on-board electronic components. ALERT-ACTIVE submode has all circuits active. Exercises are generally performed during the ALERT-ACTIVE mode. In ALERT-SLEEP submode, only the real time clock and SRAM memory remain active. ALERT-SLEEP mode is the standard mode of operation between exercise prompts. To allow switching between submodes, primary and backup battery power should be available during the ALERT mode. A beeper function can be used to prompt the patient that an exercise time has been reached.

FULL-ON mode primarily is used during programming and data transfer operations. All on-board electronics and the display are active. FULL-ON mode can be activated automatically when an interface cable is connected.

In a preferred embodiment, the controller can prompt and monitor the performance of isometric exercises, range of motion exercises, isotonic exercises and/or neurosensory, reflex, proprioception and neuromotor exercises. When the patient has suffered a stroke, preferably the exercises involve more than simple proprioception. The stroke generally destroys neurological pathways involving brain cells controlling reflexes, movements, and the like. Thus, the patient must relearn new neurological pathways connected to different memory locations. A variety of reflex exercises can be used to relearn these neurological pathways.

When the health care professional programs the controller, the desired exercises from this group of possible exercises are selected along with the associated parameters and timing conditions for the selected exercises. Also, the controller preferably can store two or more sets of exercise routine parameters that can be used in different time intervals relative to the start of rehabilitation. In other words, after a first set of exercise routines have been used for a certain period of time, the controller selects a second, generally more difficult, set of exercises for the patient to perform. These exercises can be performed for any selected joint or group of joints.

Similarly, the control unit can be programmed to prompt the patient to perform different exercises at different time of the day. These can be designed in a variety of ways by the health care professional based on the particular circumstances of the patient. For example, the control unit can prompt the patent to perform range-of-motion exercises every three hours, finger squeeze exercises every hour and longer exercise sessions for neurological rehabilitation every evening.

Preferably, the controller prompts the patient at the time for performance of the selected exercises. In some embodiments, the patient presses a key when they are ready to proceed. The display on the monitor can graphically show the patient's motions with suitable coordinates for the particular exercise and compare them with a target performance, if suitable. The controller can store all of the data points or averages over a set of exercises performed over a period of time.

To perform the isometric exercises of a particular joint, the corresponding hinge is adjusted to a particular angle. If a manual hinge is used, the hinge is manually adjusted. The controller may instruct the patient if the hinge is set at the desired angle. At the correct angle, the patient applies stress against the fixed hinge in one direction or the other. The controller instructs the patient if the applied stresses are within tolerance values of a target value. The controller preferably prompts the patient regarding the timing of the exercises, including the repetition rate and the amount of time to hold an applied stress. After the selected number of repetitions are performed the exercises are terminated or a new angle of the hinge is selected. The process is repeated until exercises are performed at all of the desired angles for the particular joint. For hinges that rotate in multiple planes, the joint can be exercised with forces applied along any plane of motion appropriate for the joint. The motion can be in a single plane at a particular time or within multiple planes simultaneously, such as moving a hand in a circle with an outstretched arm.

Improvement in joint function can be advanced with attention to achieving a desirable range-of-motion (ROM). The ROM can be monitored using the orthosis with a suitable position sensing hinge or hinges, as described above. The particular hinge is set to allow rotation, at least over a portion of the possible rotation range. For hinges that rotate in multiple planes of motion, the range-of-motion exercises can be performed in the different planes.

Proprioception in this context refers to the patient's sense of position in space, such as the bend of a particular joint. This seeming innate knowledge is a learned phenomenon involving a complex interaction of nerve sensations from sensors that are processed and combined with feedback and correction. A joint has dozens of single-celled measurement sensors: Paninian-like receptors; Ruffini corpuscles and the like. The brain and spinal cord process the information from these cellular sensors. When a joint is damaged, dozens of sensors may be permanently lost. For example, the anterior cruciate ligament of a knee has over 60 sensor/receptor cells some of which may be lost when the ligament tears. The body makes up for lost receptors by recruiting new sensor information from adjacent places. A new pathway and analysis must be relearned by the nervous system. With a properly designed orthosis this process should be accelerated and enhanced.

In one embodiment, the controller display prompts an action through a graphic display, for example, to get a ball back into a circle, and the patient must react quickly, reflexively with the rehabilitating joint in the orthosis to move the ball on the screen. The position of the ball on the screen is correlated with the position of the joint by way of the position sensor in the orthosis operably connected to the controller. By changing the position of the joint, e.g. knee, the patient can move the ball back into the circle or to another target of some kind. These exercises improve cooperation and coordination. A similar game format can be used to perform isometric exercises where the amount of strain measured by the strain gauge is used to move the cursor. For hinges/joints that rotate in multiple planes, the full range of motion can be explored in a proprioception exercise.

Isotonic exercises are similar to the range-of-motion exercises except that selected resistance is provided in the selected hinge. Resistance is provided by a manual unit, such as resistance unit 400 above, or by an electrical resistance hinge actuated by a controller, such as electromechanical hinge 240 above. In any case, a desired amount of resistance is set manually or automatically. The joint is then flexed over a prescribed range-of-motion. A controller can monitor the degree of flexing of the joint using a position sensor in the hinge and the amount of forces applied during the flexing using a strain gauge. The strain gauge can be calibrated such that a strain reading can be matched with a corresponding torque applied to the hinge.

Some preferred embodiments include an additional component to provide for closed chain exercises when used with the joint supporting component. Closed chain exercises involve muscular motion against resistance to mimic natural motions against gravity or to provide balanced stresses to the joint. Closed chain exercises can be contrasted with open chain exercises where a limb or trunk is moved or stressed in space without any resistance against the motion other than perhaps the weight of the limb itself. Closed chain exercise may provide more balanced exercise of the various muscle groups within a patient's limb or trunk. The closed chain component may or may not be physically connected with the joint supporting orthosis components.

For the performance of closed chain exercises, a body portion pushes against an essentially immovable surface. The surface can be a floor, a wall, a table top or the like. In order to monitor the forces being applied, a sensor is used that is placed between the body part and the surface, for example, the stress sensor 898 of heel support 890. If closed chain exercises are to be performed with joints other than the knee, a suitable force sensor can be used. For example, a elbow can be exercised pushing with a hand against a pad sensor on a table or against a wall. These sensors can be connected to the controller. Additional information on the performance of the exercises described above and the corresponding programming of the controller is found in the 60/098,779 application.

As noted above, the controller can be attached to a variety of additional devices, such as closed chain exercise units, energy propagating transducers and the like, to assist with treatment. Generally, the monitoring of the operation of these additional units can be performed with the controller in a straightforward manner.

The controller can be programmed to accept other input from the patient. In particular, inquiries can be directed to the patient at the start of an exercise routine, at the end of an exercise routine or at other times. The answers are stored for downloading to a health care professional along with suitable information regarding the performance of programmed exercises.

As part of the monitoring operation, the controller preferably, continuously monitors the performance of an exercise to prevent difficulties. For example, after exercises have been started, the transducer parameters are evaluated to determine if the exercises are being performed within specified parameters. If the exercises are not being performed within tolerance values, a sound warning can be given. Additional description on the performance of exercises with an instrumented orthosis are described in the 60/098,779 application.

Periodically, the information stored by the processor is downloaded to a health care professional. Various methods for downloading the information were described above. In principle, the controller can store all of the information about the performance of particular sets of exercise routines and download all of this information for analysis. Alternatively, the controller can perform some initial data analysis to reduce the amount of data that must be stored and transferred. The preliminary analysis, if any, performed by the controller can include grouping and/or averaging of groups of exercises over certain periods of time and/or performed at particular times of the day. Thus, raw or analyzed data can be transferred. This analysis can involve an evaluation of variation with the progress of time to assist the health care professional evaluate whether the patient is making sufficient improvement and to evaluate whether the exercise routine programmed into the controller is appropriate.

To reduce the chance of the patient injuring themselves using the orthoses described herein, the patient preferably is examined by a trained health care professional prior to using the orthosis. Upon evaluating the condition of the patient, the controller is programmed for suitable exercises. In preferred embodiments, a monitor station assists the health care professional with the programming process. Once the controller is connected to the monitor station by way of an RS 232 connection, a modem connection, a IR connection, a radio connection, a IR connection or other suitable connection using an appropriate protocol, the program is downloaded into the controller.

At prescribed periods of time, information stored in the controller regarding the performance of the exercises by the patient can be downloaded into the monitor station. The time interval can be determined based on the storage capacity of the controller, the suitable length for evaluation of progress by health care professional or other similar issues. The download of information from the controller to the monitor station can be performed at the health care facility where the monitor station is located or from a remote location. If performed at the health care facility, the information can be downloaded by direct hook up of the controller with the monitor station or through a modem, radio connection, infrared connection or the like. Remote hook up can be performed with a modem connection, internet connection, radio communication or other longer range connection. A combination of the downloading of performance parameters with telecommunications capability is described further in copending and commonly assigned U.S. patent application Ser. No. 09/226,866, entitled "REMOTE MONITORING OF AN INSTRUMENTED ORTHOSIS," incorporated herein by reference.

Suitable analysis is performed of the data for example, the downloaded data on the exercises can be plotted in raw form or following some form of data averaging or selection. Based on an evaluation of the downloaded data, the health care professional can maintain the exercise program in its initially programmed form or modify the exercise program to account for unexpected developments. In preferred embodiments, the health care professional can reprogram the controller remotely such that any desired changes in the routine can be made without the patient needing to visit the health care facility. Further information on performance data analysis is found in the 60/098,779 application.

One of several important functions of a microprocessor controlled orthosis is to monitor compliance with performance of exercises. A useful adjunct to the compliance monitoring function can be achieved by performing a psychological evaluation of the patient. The psychological test can be used to evaluate the suitability of the programmed exercises as well as indicate other potential problems with the healing process not directly linked to the exercises.

Specifically, patients undergoing treatment for an injury are under stress. Pain, immobility, lack of understanding, fear contribute to the stress resulting from the injury. The stress complicates recovery because the stress interacts with other emotional or physical complaints. In particular, patients under stress undergo changes in their psychology. This psychological change commonly manifests itself as depression, fear, anxiety, anger or other types of decompensation.

The stress and associated changes in psychology complicates the recovery by impairing the patient's ability to understand the problem and to cooperate fully in their own recovery. For example, depressed patients experience more pain, as measured by increased need for pain medication. Also, depressed patients exert less force during physical testing and, therefore, are measurably weaker. Thus, stress and associated complications can result in an objective, measurable decrease in physical ability.

In the past, such factors generally have been accommodated or accepted as unavoidable because there has been no way to follow easily or to evaluate reasonably the changes in the patient's mental state. The ability to monitor the patient's mental emotional state can lead to important advances in the treatment of orthopedic injuries. To make effective use of the information on the patient's emotional state, the information preferably is coordinated with other aspects of the orthopedic and neurological recovery.

As a result of their injury, patients likely will undergo a predictable series of changes as they first adapt to the pain of their injury, the inconvenience, the expense and the change in their function. The patient's emotional changes likely will include aspects of denial, anger, bargaining, acceptance, etc., which have also been associated with death and dying, as described by Elisabeth Kubler-Ross. For a more complete description of these emotional changes see "On Death and Dying," Elisabeth Kubler-Ross, Simon & Schuster (1969), incorporated herein by reference. These changes can be correlated with predictable or identifiable factors, such as age, gender, mechanism and socio-economic status.

The emotional changes are a form of psychological pain. Since it is known that patients will undergo these emotional changes, a more complete treatment of the patient includes the management of the emotional changes accompanying the physical trauma. Effective management and/or treatment of the emotional changes preferably would involve 1) education, 2) monitoring, 3) accurate characterization, 4) cooperation-based contingent intervention, and 5) communication.

In analogy with Kubler-Ross models, patients can benefit from the simple knowledge that emotional changes are common and predictable. Reassuring information can be passed along to the patient at regular intervals, consistent with identifiable patient demographic parameters. Patient suffering is reduced by mental preparation. The educational data can only be presented with optimum timing if the patient's ability to absorb the information is known. Thus, individual specific and time specific psychological quantification can be used to considerable advantage. Psychological quantification can be accomplished efficiently through portable psychological testing coordinated with the patient's physical therapy or exercise prescription. In particular, appropriate educational information can be presented by the controller.

As part of the monitoring function, the treating professional preferably knows what the patient is experiencing and when they are experiencing it. These experiences will be based on the patient's specific stresses, demands, events and individual psychology. The experiences also will parallel progress or relapse in the orthopedic treatment regime. While qualitative features of the patient's emotional responses may be predictable, it is difficult to know when the psychological treatment can be effectively provided. By analogy, with physical discomfort the specific timing of effective administration of pain medication, assistance with physical activities and nursing assistance is highly variable and patient specific. The treatment is more effective when the patient is able to say when they require pain medication or other forms of help.

Monitoring is an important component to effective treatment. Effective monitoring is not possible without ongoing, systematic and injury appropriate querying of the patient. To perform this in a cost effective way, the monitoring function must be portable with the patient. This portable monitoring can be accomplished by incorporating psychological monitoring on an orthopedic management system, such as those described herein. In particular, the monitoring function can be coordinated by the controller, which is programmed to pose questions and to receive answers from the patient. The psychological monitoring can be used to modify parameters in the orthopedic management, such as device comfort, exertion levels and pain control, when the monitoring function detects deviations from an expected emotional or psychological condition.

To obtain an accurate characterization of the patient's emotional state, the treating professional and the patient need to work together to determine the stage of the patient's emotional recovery, the depth and type of the patient's distress, and changes in the patient's emotional condition as the problem either resolves or worsens. There are a number of literature based instruments available that have been used to characterize patients on a one-time basis to quantify an emotional state. These instruments can be adapted to an ongoing monitoring of a constantly evolving medical-surgical state, such as associated with an orthopedic or neurological injury.

A first instrument for emotional evaluation involves the formation of a pain diagram. The patient is asked if the pain occurs at the expected location. Pain away from the expected location may indicate a complication or missed injury. See the discussion in Mayer et al., "A Prospective Short-Term Study of Chronic Low Back Pain Patients Utilizing Novel Objective Functional Measurement, Pain 25:53-68 (1986), incorporated herein by reference.

An alternative approach is known as the Million analog scale. The patient is asked to characterize their discomfort based on a range of possible limitations. For example, they may be asked to state on an arbitrary scale their perceived functional restriction from "no pain" to "worst possible pain." In addition, they may be asked whether they are easily able to work, unable to work or some gradation between these limits. The responses generally change based on the patient's recovery process and their perception of their recovery process. Thus, this is a straightforward tool to regularly administer during high risk periods as a significant tool to report changes in the patient's condition. For further discussion of this approach see, for example, R. Million et al., "Assessment of the Progress of the Back-Pain Patient," Spine, 7(3):204-212 (1982), incorporated herein by reference.

Patient's often find it difficult to describe their symptoms. In addition, patients in a certain high risk category for back injury are likely to have a range of educational limitations. This is a paradox that the patients who are most likely to sustain a certain type of injury are also least likely to be able to adequately characterize it as needing and deserving treatment. The McGill Pain Questionnaire provides a tool to overcome these difficulties. The McGill Pain Questionnaire uses words that the patient can understand and appropriately choose, but words that the patient would not likely use without suggestion. The words are provided in a format and grouping that tells more about the patient's, situation and emotional state than just their pain level. A further description of the McGill Pain Questionnaire is described in R. Melzack, "The McGill Pain Questionnaire Major Properties and Scoring Methods," Pain 1:277-299 (1975), incorporated herein by reference. The questionnaire can be updated and modified as appropriate.

Another potential instrument is the Beck Depression Inventory (BDI). Depression often follows injury and states of pain. A method of polling the patient for signs of depression would be another useful method of controlling and improving the recovery process, as the patient progresses through their disease process.

The BDI is a series of questions whose answers reflect the patient's mental state with respect to indications of depression. The BDI provides a standardized, objective measure that approximates clinical judgments of the intensity of depression without variability due to an evaluator's idiosyncrasies or theoretical orientation. The BDI's ease of administration and low cost provide for its economical use, for example, with a patient suffering from an orthopedic injury. Furthermore, statistical analysis can be performed with the quantitative data generated by the BDI.

In its standard form, the BDI consists of 21 items that are scored to assess the patient's state of depression. Each of the 21 items can be rated on a scale of 0-3 such that the total score ranges from 0-63. The patient selects the number next to a statement that reflects the way that he/she has felt over a selected time period. The degree of depression is evaluated by the sum of the individual numbers with totals indicating as follows: 0-9 no depression, 10-16 mild depression, 17-29 moderate depression and 30-63 severe depression. In the standard test, the 21 items are: 1) sadness, 2) pessimism, 3) failure, 4) dissatisfaction, 5) guilt, 6) punishment, 7) self-dislike, 8) self-accusations, 9) suicidal thought, 10) crying, 11) irritability, 12) withdrawal, 13) indecision, 14) self-image, 15) work inhibition, 16) insomnia, 17) fatigue, 18) anorexia, 19) weight loss, 20) hypochondria, 21) libido loss.

In summary, these instruments can be used 1) to demonstrate the location of pain as typical or atypical (the pain diagram), 2) to evaluate the patient's own perceived level of disability (the million analog scale), 3) to describe the specific nature of the pain as stinging, burning, torturing, or the like (the McGill Pain Questionnaire), or to reflect the effect of the difficulties on the patient's mental state (Beck Depression Inventory). Suitable tests are described further in the 60/098, 779 application. Thus, standardized instruments for emotional evaluation can be integrated into an orthopedic treatments regime organized around an instrumented orthosis.

In particular, the questions can be posed and the answers received through the controller. These questions can be posed at regular intervals. The questions can be interspersed throughout the day and coordinated with the timing of exercise routines. In particular, different subset of questions can be asked at different times. For example, a subset of questions on pain levels can be asked in the morning while a subset of questions on depression can be asked in the afternoon. To assist with these tests, the controller can be attached to a television set to provide a larger display, if desired. If administered in an appropriate and timely manner, the subjective aspects of the patient's suffering can be identified and quantified for appropriate intervention.

The psychological test can be integrated with the physical evaluation of the patient to form a more complete overall evaluation. Using this evaluation, the exercise routine can be modified in response partly to the to mental attitude of the patient to help assure further compliance with the exercises and to increase the comfort level of the patient. The balance of all of these factors can lead to faster rehabilitation of the patient.

The patient's ability to cooperate with their treatment is determined by their emotional state. Like physical pain, the patient's emotional state changes in a highly individualized manner. If the patient's emotional state can be more scientifically evaluated, characterized and bracketed with identifiable ranges and types, the modification to a more effective or more pleasurable reinforcement scheme can be assisted through cooperation-based contingent intervention. In particular, the information received from the patient is used to improve the cooperation of the patient in their own recovery. Thus, the relationship between the patient and the treating professional is augmented in a way that strengthens the relationship without adding unreasonable cost to treatment.

With respect to implementing the cooperation-based contingent intervention, the controller first evaluates the immediacy of the patient's state. If there are serious concerns, such as if the patient indicates that the pain is unbearable or tortuous or if the patient is seriously depressed, the controller can either instruct the patient to immediately call the doctor or directly interface with the health professional's computer to down load the information, with the patient's help, if needed. Alternatively, the controller can modify the exercise level by decreasing the exertion if the pain is higher than desired or increase the level if the pain is low and the patient is frustrated by the slow pace.

Thus, the patient's physical and mental condition, as communicated in the psychological evaluation, can provide useful information regarding the modifications to the treatment program in response to the patient's evolving physical condition and the mental state of the patient. Cooperation-based contingent intervention involves integrating the result of the psychological evaluation to the patient's evolving physical abilities to provide for improved adjustment of the treatment program. For example, a variety of different formats for presenting a particular exercise can be tried to evaluate whether the patient is more receptive to the particular formats. The formats can be put in the form of a game or in the form of detailed instructions with continuous positive reinforcement.

Communication with the health care professional is an important aspect of the process. The controller can be used to intervene in the communication process to ensure that important information is communicated in a timely way. Regardless of any immediate concerns, the outcome of the patient's responses are reported to the treating professional for confirmation, data analysis and other types of support. Prior to evaluation by the health care professional, the patient's responses are characterized and identified. This can be done by the controller or by a remote processor. A scientific and quantifiable method of evaluating emotional change is an important component of the evaluation process.

As a supplement to or as an alternative to, the questioning of the patient regarding their emotional state, physiological measurements can be made regarding conditions correlated with stress. For example, pulse rate can be measured with, for example, a laser Doppler sensor or a pulse oximeter. A pulse oximeter is an apparatus that the patient inserts their finger into to measure pulse rate and blood oxygenation. Similarly, galvanic skin response can be measured using electrodes placed on the skin. The electric resistance of skin is measured with the electrodes. In addition, blood pressure can be measured with a blood pressure cuff. These physiological measurements can be controlled and monitored with the controller. The physiological measurements can then be downloaded to the health care provider.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. An instrumented orthosis comprising:
an ambulatory support that fits around a joint of a patient, the support comprising a hinge that can rotate in several different planes supporting the respective body portions connected at the joint, wherein the support is configured to brace the joint when placed on the patient;
position sensing elements operably connected to the hinge, wherein the position sensing elements measure rotational motions in different planes about the joint; and
an ambulatory control unit operably connected to the position sensing element to receive signals related to the position of the hinge, the control unit comprising a microprocessor and a display, wherein the control unit is programmed to automatically select a target range of motion from a set of a target range of motion designated by a health care professional and prompt the patient to perform the selected target range of motion under certain circumstances based on an analysis of the patient's circumstances, wherein the microprocessor is programmed to compare the actual range of motion about the joint performed by the patient with the target range of motion for the joint and stores data points from measurements of the signals, wherein the microprocessor provides output to the display in which the display shows at prescribed times the difference between the actual range of motion about the joint and the target range of motion for the joint.

2. The orthosis of claim 1 wherein the support fits around the shoulder of a patient.

3. The orthosis of claim 2 wherein a hinge provides for the motion of an arm generally in a plane defined by the patient's torso.

4. The orthosis of claim 2 wherein a hinge provides or the motion of an arm generally from the front of the patient to the back of the patient.

5. The orthosis of claim 2 wherein a hinge provides for the motion of an arm involving rotation of the fore arm relative to the shoulder.

6. The orthosis of claim 1 wherein the support fits around the hip of a patient.

7. The orthosis of claim 1 wherein the support fits around the thumb of a patient.

8. The orthosis of claim 1 wherein the hinge that can move in several different planes comprises a plurality of hinges that can move separate planes, where each hinge is on a lever arm of the other hinge.

9. The orthosis of claim 1 wherein the hinge is lockable hinge such that application of the lock prevents motion in all planes.

10. The orthosis of claim 1 further comprising strain gauges connected to the support such that the strain within the support is measured by the strain gauge.

11. The orthosis of claim 1 wherein the position sensing elements comprises a variable resistor, wherein the resistance varies with the orientation of the hinge.

12. A method of rehabilitating a joint that has a range of motion in a plurality of planes, the method comprising exercising with an orthosis of claim 1.

13. An orthosis comprising:
an ambulatory support that fits around a plurality of joints of a patient, the support comprising a plurality of hinges such that motions about separate hinges correspond to motions about different joints with the support supporting the respective body portions connected at the individual joints;
position sensors operably connected with the hinges such that motion can be measured about different joints; and
a control unit operably connected to the position sensors to receive signals related to the position of the hinges, the control unit comprising a microprocessor and a display, wherein the control unit is programmed to automatically select a target range of motion from a set of a target range of motion designated by a health care professional and prompt the patient to perform the selected target range of motion under certain circumstances based on an analysis of the patient's circumstances, wherein the microprocessor is programmed to compare the actual range of motion performed by the patient about a particular joint with the target range of motion for the joint and stores data points from measurements of the signals and wherein the microprocessor provides output to the display in which the display shows at prescribed times the difference between the range of motion about the particular joint and the target range of motion for the joint.

14. The orthosis of claim 13 wherein the support further comprises an additional hinge such that a plurality of hinges respond to separate rotational motions about a single joint.

15. The orthosis of claim 13 wherein the support comprises a full leg brace and a shoulder brace.

16. The instrumented orthosis of claim 1 wherein the control unit has a port for downloading the stored signals.

17. The instrumented orthosis of claim 1 wherein the control unit comprises a radio transmitter.

18. The instrumented orthosis of claim 1 wherein the control unit comprises a radio receiver.

19. The instrumented orthosis of claim 1 wherein the control unit comprises a program that can perform a data analysis on the signals.

20. The instrumented orthosis of claim 13 wherein the control unit has a port for downloading the stored signals.

21. The instrumented orthosis of claim 13 wherein the control unit comprises a radio transmitter.

22. The instrumented orthosis of claim 13 wherein the control unit comprises a radio receiver.

23. The instrumented orthosis of claim 13 wherein the wherein the control unit comprises a program that can perform a data analysis on the signals.

* * * * *